US009903871B2

(12) United States Patent
Chang et al.

(10) Patent No.: US 9,903,871 B2
(45) Date of Patent: Feb. 27, 2018

(54) STABILIZED PEPTIDE FRAGMENTS FROM NUCLEOREDOXIN X1 AND USES THEREOF

(71) Applicant: Temple University of the Commonwealth System of Higher Education, Philadelphia, PA (US)

(72) Inventors: Frank N. Chang, Dresher, PA (US); George P. Tuszynski, Pittsgrove, NJ (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 14/800,162

(22) Filed: Jul. 15, 2015

(65) Prior Publication Data

US 2016/0018403 A1   Jan. 21, 2016

Related U.S. Application Data

(60) Provisional application No. 62/024,733, filed on Jul. 15, 2014.

(51) Int. Cl.
| | |
|---|---|
| G01N 33/574 | (2006.01) |
| G01N 33/563 | (2006.01) |
| G01N 33/577 | (2006.01) |
| C07K 16/40 | (2006.01) |

(52) U.S. Cl.
CPC ....... *G01N 33/57488* (2013.01); *C07K 16/40* (2013.01); *C07K 2317/21* (2013.01); *C07K 2317/24* (2013.01); *C07K 2317/34* (2013.01); *C07K 2317/76* (2013.01); *G01N 2333/902* (2013.01); *G01N 2333/908* (2013.01); *G01N 2800/52* (2013.01)

(58) Field of Classification Search
None
See application file for complete search history.

(56) References Cited

U.S. PATENT DOCUMENTS

| 7,326,326 | B2 | 2/2008 | Chang | |
|---|---|---|---|---|
| 8,420,333 | B2 | 4/2013 | Chang | |
| 2003/0108965 | A1* | 6/2003 | Schummer | C07K 14/811 435/7.23 |
| 2004/0005563 | A1* | 1/2004 | Mack | C07K 14/47 435/6.14 |
| 2004/0213791 | A1* | 10/2004 | Bander | A61K 47/48638 424/155.1 |
| 2006/0104902 | A1 | 5/2006 | Powis | |
| 2006/0269921 | A1* | 11/2006 | Segara | C12Q 1/6886 435/6.16 |
| 2007/0059806 | A1* | 3/2007 | Arnon | C12N 15/115 435/91.1 |
| 2009/0148464 | A1 | 6/2009 | Yodoi | |
| 2009/0280995 | A1 | 11/2009 | Ferguson | |
| 2011/0143379 | A1 | 6/2011 | Graham | |
| 2012/0015847 | A1 | 1/2012 | Kim | |

FOREIGN PATENT DOCUMENTS

| WO | WO2004/032838 | * | 4/2004 |
|---|---|---|---|
| WO | 2008018642 | | 2/2008 |
| WO | 2009014552 | | 1/2009 |
| WO | 2011008746 | | 1/2011 |

OTHER PUBLICATIONS

Paul, Fundamental Immunology, 3rd Edition, 1993, pp. 292-295.*
Bendig M. M. (Methods: A Companion to Methods in Enzymology, 1995; 8:83-93).*
Funato (Current Biology, vol. 20, p. 1945-1952, 2010).*
Fraker (Biol. Cell, vol. 101, p. 431-440, 2009).*
Bordier, J., "Phase separation of integral membrane proteins in Triton X-114 solution," Feb. 25, 1981, pp. 1604-1607, vol. 256(4), The Journal of Biological Chemistry.
Ceccarelli, J., et al., "The redox state of the lung cancer microenvironment depends on the levels of thioredoxin expressed by tumor cells and affects tumor progression and response to prooxidants," 2008, pp. 1770-1778, vol. 123, International Journal of Cancer.
Chaiswing, L., et al., "Characterization of redox state of two human prostate carcinoma cell lines with different degrees of aggressiveness," Jul. 2007, pp. 202-215, vol. 43(2), Free Radical Biology and Medicine (abstract only).
Cole-Ezea, P., et al., "Glutathione peroxidase 4 has a major role in protecting mitochondria from oxidative damage and maintaining oxidative phosphorylation complexes in gut epithelial cells," Aug. 1, 2012, pp. 488-497, vol. 53(3), Free Radical Biology and Medicine (abstract only).
Corthals, GL., et al., "The dynamic range of protein expression: a challenge for proteomic research," Apr. 2000, pp. 1104-1115, vol. 21(6), Electrophoresis (abstract only).
Dennis, M., et al., "Albumin binding as a general strategy for improving the pharmacokinetics of proteins," Jul. 15, 2002, pp. 35035-35043, vol. 277(38), The Journal of Biological Chemistry.
Dewhirst, M., "Relationships between cycling hypoxia, HIF-1, angiogenesis and oxidative stress," Dec. 2009, pp. 653-665, vol. 172(6), Radiation Research.
Farina, A., et al., "Thioredoxin alters the matrix metalloproteinase/ tissue inhibitors of metalloproteinase balance and stimulates human SK-N-SH neuroblastoma cell invasion," 2001, pp. 405-413, vol. 268, European Journal of Biochemistry.
Funato, Y., et al., "Nucleoredoxin sustains Wnt/Beta-Catenin signaling by retaining a pool of inactive dishevelled protein," Nov. 9, 2010, pp. 1945-1952, vol. 20(21), Current Biology.

(Continued)

*Primary Examiner* — Michael Allen
(74) *Attorney, Agent, or Firm* — RatnerPrestia

(57) ABSTRACT

An embodiment of the invention relates to the use of stabilized cancer peptide fragments derived from "redoxin proteins" selected from the group consisting of thioredoxin; peroxiredoxin-1, 2 and 3; glutaredoxin-3; glutathione peroxidase-4; and nucleoredoxins for the diagnosis of cancers, particularly pancreatic cancer. A method for the detection of cancer, severity of cancer, and/or effectiveness of a therapeutic regimen comprises detecting and/or measuring the amount of redoxin peptide fragments present in the biological sample of a subject.

8 Claims, 8 Drawing Sheets

(56) References Cited

OTHER PUBLICATIONS

Hanschmann, E.M., et al., "Thioredoxins, glutaredoxins, and peroxiredoxins—molecular mechanisms and health significance: from cofactors to antioxidants to redox signaling," 2013, pp. 1539-1605, vol. 19(13), Antioxidants & Redox Signaling.

Ishii, T., et al., "Novel roles of peroxiredoxins in inflammation, cancer and innate immunity," Mar. 2012, pp. 91-105, vol. 50(2), Journal of Clinical Biochemistry and Nutrition.

Karlenius, T.C., et al., "Thioredoxin and Cancer: A role for thioredoxin in all states of tumor oxygenation," Mar. 25, 2010, pp. 209-232, vol. 2, Cancers.

Lillig, C.H., et al., "Glutaredoxin systems," Nov. 2008, pp. 1304-1317, vol. 1780(11), Biochimica et Biophysica Acta (BBA) (abstract only).

Lowenthal, M., et al., "Analysis of albumin-associated peptides and proteins from ovarian cancer patients," 2005, pp. 1933-1945, vol. 51(10), Clinical Chemistry.

Luczaj, W., et al., "DNA damage caused by lipid peroxidation products," Apr. 16, 2003, pp. 391-413, vol. 8(2), Cellular and Molecular Biology Letters.

Merrell, K, et al., "Analysis of low-abundance, low-molecular-weight serum proteins using mass spectrometry," Dec. 2004, pp. 238-248, vol. 15(4), Journal of Biomolecular Techniques.

Moradi, M., et al., "Plasma selenium concentration and glutathione peroxidase activity in breast cancer patients before and after chemotherapy," Summer 2008, pp. 119-122, vol. 1(3), Iranian Journal of Cancer Prevention.

O'Farrell, P.H., "High resolution two-dimensional electrophoresis of proteins," Sep. 5, 1974, pp. 4007-4021, vol. 250(10), The Journal of Biological Chemistry.

Riddell, J.R., et al., "Peroxiredoxin 1 controls prostate cancer growth through toll-like receptor 4-dependent regulation of tumor vasculature," Feb. 22, 2011, pp. 1637-1646, vol. 71(5), Cancer Research.

Schneider, M., et al., "Absence of glutathione peroxidase 4 affects tumor angiogenesis through increased 12/15-lipoxygenase activity," Mar. 2010, pp. 254-263, vol. 12(3), Neoplasia.

Soga, M., et al., "Oxidative stress-induced diseases via the ASK1 signaling pathway," Mar. 5, 2012, pp. 1-5, Article ID 439587, International Journal of Cell Biology.

Song, I.S., et al., "Mitochondrial Peroxiredoxin III is a potential target for cancer therapy," Oct. 21, 2011, pp. 7163-7185, vol. 12, International Journal of Molecular Sciences.

Utomo, A., et al., "Identification of a novel putative non-selenocysteine containing phospholipid hydroperoxide glutathione peroxidase (NPGPx) essential for alleviating oxidative stress generated from polyunsaturated fatty acids in breast cancer cells," Aug. 4, 2004, pp. 43522-43529, vol. 279(42), The Journal of Biological Chemistry.

Vaquero, E.C., et al., "Reactive oxygen species produced by NAD(P)H oxidase inhibit apoptosis in pancreatic cancer cells," May 23, 2004, pp. 34643-34654, vol. 279(33), The Journal of Biological Chemistry.

Vasseur, S., et al., "Hypoxia induced tumor metabolic switch contributes to pancreatic cancer aggressiveness," Dec. 16, 2010, pp. 2138-2152, vol. 2, Cancers.

Zheng, X., et al., "G-protein coupled receptor-associated sorting protein 1 (GASP-1), a ubiquitous tumor marker," Aug. 2012, pp. 111-115, vol. 93(1), Experimental and Molecular Pathology (abstract only).

Chen, G. et al., "Different Redox States in Malignant and Nonmalignant Esophageal Epithelial Cells and Differential Cytotoxic Responses to Bile Acid and Honokiol," Antioxidants & Redox Signaling, 2009, vol. 11, No. 5, pp. 1083-1095.

International Search Report and Written Opinion of the International Searching Authority for International Application No. PCT/US2015/040556 dated Oct. 15, 2015.

\* cited by examiner

```
         10         20         30         40         50
MVKQIESKTA FQEALDAAGD KLVVVDFSAT WCGPCKMIKP FFHSLSEKYS
         60         70         80         90        100
NVIFLEVDVD DCQDVASECE VKCMPTFQFF KKGQKVGEFS GANKEKLEAT INELV
```

FIG. 2

```
                              10         20         30         40         50
                     MSSGNAKIGH PAPNFKATAV MPDGQFKDIS LSDYKGKYVV FFFYPLDFTF
                              60         70         80         90        100
                     VCPTEIIAFS DRAEEFKKLN CQVIGASVDS HFCHLAWVNT PKKQGGLGPM
                             110        120        130        140        150
                     NIPLVSDPKR TIAQDYGVLK ADEGISFRGL FIIDDKGILR QITVNDLPVG
                             160        170        180        190
                     RSVDETLRLV QAFQFTDKHG EVCPAGWKPG SDTIKPDVQK SKEYFSKQK
```

FIG. 3

MASGNARIGK PAPDFKATAV VDGAFKEVKL SDYKGKYVVL FFYPLDFTFV
CPTEIIAFSN RAEDFRKLGC EVLGVSVDSQ FTHLAWINTP RKEGGLGPLN
IPLLADVTRR LSEDYGVLKT DEGIAYRGLF IIDGKGVLRQ ITVNDLPVGR
SVDEALRLVQ AFQYTDEHGE VCPAGWKPGS DTIKPNVDDS KEYFSKHN

FIG. 4

```
         10          20          30          40          50
MAAAVGRLLR  ASVARHVSAI  PWGISATAAL  RPAACGRTSL  TNLLCSGSSQ
         60          70          80          90         100
AKLFSTSSSC  HAPAVTQHAP  YFKGTAVVNG  EFKDLSLDDF  KGKYLVLFFY
        110         120         130         140         150
PLDFTFVCPT  EIVAFSDKAN  EFHDVNCEVV  AVSVDSHFSH  LAWINTPRKN
        160         170         180         190         200
GGLGHMNIAL  LSDLTKQISR  DYGVLLEGSG  LALRGLFIID  PNGVIKHLSV
        210         220         230         240         250
NDLPVGRSVE  ETLRLVKAFQ  YVETHGEVCP  ANWTPDSPTI  KPSPAASKEY

FQKVNQ
```

FIG. 5

```
         10         20         30         40         50
MAAGAEAAV AAVEEVGSAG QFEELLRLKA KSLLVVHFWA PWAPQCAQMN
         60         70         80         90        100
EVMAELAKEL PQVSFVKLEA EGVPEVSEKY EISSVPTFLF FKNSQKIDRL
        110        120        130        140        150
DGAHAPELTK KVQRHASSGS FLPSANEHLK EDLNLRLKKL THAAPCMLFM
        160        170        180        190        200
KGTPQEPRCG FSKQMVEILH KHNIQFSSFD IFSDEEVRQG LKAYSSWPTY
        210        220        230        240        250
PQLYVSGELI GGLDIIKELE ASEELDTICP KAPKLEERLK VLTNKASVML
        260        270        280        290        300
FMKGNKQEAK CGFSKQILEI LNSTGVEYET FDILEDEEVR QGLKAYSNWP
        310        320        330
TYPQLYVKGE LVGGLDIVKE LKENGELLPI LRGEN
```

FIG. 6

```
              10         20         30         40         50
         MSLGRLCRLL KPALLCGALA APGLAGTMCA SRDDWRCARS MHEFSAKDID
              60         70         80         90        100
         GHMVNLDKYR GFVCIVTNVA SQUGKTEVNY TQLVDLHARY AECGLRILAF
             110        120        130        140        150
         PCNQFGKQEP GSNEEIKEFA AGYNVKFDMF SKICVNGDDA HPLWKWMKIQ
             160        170        180        190
         PKGKGILGNA IKWNFTKFLI DKNGCVVKRY GPMEEPLVIE KDLPHYF
```

FIG. 7

Nucleoredoxin Isoform 1 (SEQ ID NO: 43)

```
  1 msgfleellg eklvtgggee vdvhslgarg isllglyfgc slsapcaqls aslaafygrl
 61 rgdaaagpgp gagagaaaep eprrleivf vssdqdqrqw qdfvrdmpwl alpykekhrk
121 lklwnkyris nipsliflda ttgkvvcrng llvirddpeg lefpwgpkpf reviagpllr
181 nngqslesss legshvgvyf sahwcppcrs ltrvlvesyr kikeagqnfe iifvsadrse
241 esfkqyfsem pwlavpytde arrsrlnrly giggiptlim ldpqgevitr ggrvevlnde
301 dcrefpwhpk pvleisdsna aqlnegpclv lffvgeddge seaakqligp iaekiiakyk
361 akeeeapllf fvageddmtd slrdytnlpe aaplltlldm sarakyvmdv eeitpaivea
421 fvndflaekl kpepi
```

Nucleoredoxin Isoform 2 (SEQ ID NO: 44)

```
  1 madvsihrnp atlklwnkyr isnipslifl dattgkvvcr ngllvirddp eglefpwgpk
 61 pfreviagpl lrnngqsles sslegshvgv yfsahwcppc rsltrvlves yrkikeagqn
121 feiifvsadr seesfkqyfs empwlavpyt dearrsrlnr lygigginptl imldpqgevi
181 trggrvevln dedcrefpwh pkpvleisds naaqlnegpc lvlffvgedd geseaakqli
241 qpiaekiiak ykakeeeapl lffvageddm tdslrdytnl peaaplltli dmsarakyvm
301 dveeitpaiv eafvndflae klkpepi
```

Nucleoredoxin Isoform X1 (SEQ ID NO: 45)

```
  1 msgfleellg eklvtgggee vdvhslgarg isllglyfgc slsapcaqls aslaafygrl
 61 rgdaaagpgp gagagaaaep eprrleivf vssdqdqrqw qdfvrdmpwl alpykekhrk
121 lklwnkyris nipslifda ttgkvvcrng llvirddpeg lefpwgpkpf reviagpllr
181 nngqslesss legshvgvyf sahwcppcrs ltrvlvesyr kikeagqnfe iifvsadrse
241 esfkqyfsem pwlavpytde arrsrlnrly giggiptlim ldpqgevitr ggrvevlnde
301 eeeapllf fvageddmtd slrdytnlpe aaplltlldm sarakyvmdv eeitpaivea
361 fvndflaekl kpepi
```

FIG. 8

STABILIZED PEPTIDE FRAGMENTS FROM NUCLEOREDOXIN X1 AND USES THEREOF

CROSS-REFERENCE TO RELATED APPLICATIONS

This application claims the benefit of priority of U.S. Provisional Application No. 62/024,733, filed Jul. 15, 2014, the contents of which application are incorporated by reference herein, in their entireties and for all purposes.

FIELD OF THE INVENTION

The present invention relates to the use of stabilized peptide fragments derived from "redoxin proteins" as early or late stage cancer biomarkers. Such biomarkers can be used to determine a diagnosis or prognosis, or to assess the effectiveness of a therapeutic intervention.

BACKGROUND OF THE INVENTION

Biomarker research has exploded, primarily due to the use of proteomics approaches focusing on identifying differences in protein structure and abundance between diseased and normal states. Once identified, these biomarker proteins can be utilized for developing diagnostic tools, and because they are functional molecules, they are also more likely to be valid therapeutic targets.

The accessibility and presence of a large number of proteins in blood plasma make it an excellent matrix in which to search for new biomarkers. However, the estimated dynamic range of various protein concentrations in human serum is up to almost 10 orders of magnitude (Corthals et al., 2000), making the rapid identification of individual disease-associated proteins a tremendous analytical challenge. While total serum protein concentration is approximately 70-90 mg/ml, most useful biomarkers, such as cytokines and prostate specific antigen, are present in the nano to picogram/ml range, and disease-specific changes can be expected to be incrementally small, especially in the early stages of disease (Merrell et al., 2004). Compounding these problems, many disease-specific proteins (e.g. cancer biomarker proteins) are degraded inside the cancer cell by proteolytic enzymes, generating peptide fragments that are subsequently released into the blood. Being low molecular weight in nature, these peptide fragments generally have a half-life of only about two to four hours and most of them are cleared from circulation by the kidney (Lowenthal et al., 2005).

In order to overcome challenges presented by low concentration and rapid turnover of potentially useful cancer peptide fragments, the albumin-associated fraction of proteins and peptides has been investigated as a source of useful new disease-specific biomarkers. Albumin, the most abundant plasma protein (40-50 mg/ml), functions as a scaffold for binding small molecules, lipids, peptides and proteins in the extracellular space. It has been found to form complexes with peptide hormones such as insulin and glucagon; bradykinin, serum amyloid A, interferons, the amino terminal peptide of HIV-1, gp41, and the 14-kDa fragment of streptococcal protein G, among others. Interestingly, it was found that a small percentage of the secreted peptide fragments from degraded cancer proteins have high affinity for serum albumin and form new serum albumin complexes which increase their half-life to about 19 days rather than 2 to 4 hours if they are freely circulating in the blood (Lowenthal et al., 2005). Thus, by their association with serum albumin to form complexes, the longevity of these cancer peptide fragments can be increased by more than 100-fold (Dennis et al., 2002). Due to its high affinity for such a diverse range of ligands, the serum albumin population is expected to be highly heterogeneous, most likely comprising hundreds of different albumin complexes.

Even the most widely used technology for protein separation, 2-dimensional polyacrylamide gel electrophoresis (2-D PAGE), introduced by O'Farrell (1975), cannot separate serum albumin complexes, as it is typically conducted under "denaturing" conditions. Additionally, 2-D PAGE has many other shortcomings including requiring large amounts of samples (about 50 to 100 µg of protein per experiment) and producing a rather streaky and mostly diffused profile when serum sample is analyzed. Furthermore, proteins separated by 2-D PAGE are required to be "blotted" or transferred onto blotting membranes such as polyvinylidene difluoride (PVDF) for Western blot analysis. The efficiency of protein blotting is also variable.

As described in WO 2011/008746, the present inventors developed a new electrophoresis procedure that separates serum protein complexes directly on the PVDF membrane, thus bypassing the cumbersome, time-consuming gel electrophoresis and its subsequent blotting steps (Chang and Yonan, 2008; Chang et al., 2009). The separation of albumin complexes in the present inventors' 2-D High Performance Liquid Electrophoresis (2-D HPLE) is based on their net charge or isoelectric points (pI). The association of a newly released cancer peptide fragment with a pre-existing albumin complex changes its pI and this new albumin complex migrates to a different location on the PVDF membrane, allowing its detection among hundreds of already present albumin complexes. Because it focuses on disease specific peptide fragments, the technique enables not only the identification of new cancer protein biomarkers, but also identifies the cancer peptide motifs within these proteins. When LC-MS/MS analysis is preceded by fraction separation using 2-D HPLE, its dynamic range is enhanced to the $10^{10}$ range required for detecting low copy number cancer biomarkers, a sensitivity that has not previously been achieved using other protein separation techniques.

In the United States, pancreatic cancer is the fourth leading cause of cancer-related death in both men and women. It is estimated by the National Cancer Institute that in 2015 more than 48,000 people in the United States will be diagnosed with pancreatic cancer and more than 40,000 will die of this disease. Pancreatic cancer incidence and mortality rates are higher in men than in women. African Americans also have higher rates of pancreatic cancer incidence and mortality than whites or other racial/ethnic groups.

Early stage pancreatic cancer is asymptomatic, and there is no routine screening test for pancreatic cancer. Because pancreatic cancer usually is diagnosed at an advanced stage, the survival rate is extremely low compared with those of many other cancer types. At this time, cancer of the pancreas can be cured only when it is found at an early stage (before it has spread) and only if surgery can completely remove the tumor. Standard treatments for pancreatic cancer include surgery, radiation therapy, chemotherapy, and targeted therapy. It is estimated that approximately $2.3 billion is spent in the United States each year on pancreatic cancer treatment. Serum biomarkers for early detection of pancreatic and other cancers are urgently needed and they will save lives.

It is known that many rapidly growing tumors, including pancreatic cancer, readily become hypoxic due to the inability of the local vasculature to supply an adequate amount of oxygen (Vasseur et al., 2012). The decreased level of oxygen leads to the activation of Hypoxia-inducible transcription factor (HIF-1), which in turn induces processes such as angiogenesis (Dewhirst, 2009). Although angiogenesis occurs in nearly all human solid tumors, it does not occur in an efficient manner, leading to spatial and temporal inadequacies in delivery of oxygen. Therefore, some regions of the tumor may exhibit chronic hypoxia, while other regions of the tumor may undergo cycling hypoxia, by switching between hypoxia and re-oxygenation conditions due to irregular flow of oxygen. The re-oxygenation phase following hypoxia inadvertently causes oxidative stress. Thus, both oxidative stress and hypoxia are common features of tumors that they must deal with.

Oxidative stress is considered as one of the most important risk factors for many diseases in humans, including cancer. Often the oxidative damage resulting from oxidants such as superoxide radicals, hydroxyl radicals, and hydrogen peroxide is found in proteins, lipids and nucleic acids. In proteins, thiol groups are most reactive and easily oxidized to affect enzyme activity or cellular function. Mammalian cells have a battery of oxidation defense systems, including small molecules such as glutathione (GSH) and vitamin E that neutralize the oxidants, and enzymes specialized in oxidant detoxification, such as glutathione peroxidase, glutathione S-transferase and superoxide dismutase. Cancer cells utilize several distinct antioxidant systems to defend themselves against the high oxidative and hypoxic stresses. Antioxidants are molecules that counteract excessive ROS production by preventing or reducing the oxidation of ROS targets. For example, high level expression of antioxidant proteins derived from both thioredoxin and glutaredoxin systems are found in many cancer cells in dealing with ROS induced apoptosis (Karlenius and Tonissen, 2010)

It is also known that free radical induced lipid peroxidation causes a loss of cell homeostasis by modifying the structure and functions of cell membrane. The most important characteristic of lipid peroxidation is to cause the formation of DNA-malondialdehyde (DNA-MDA) adducts by interaction with cellular DNA (Łuczaj and Skrzydlewska, 2003). Malondialdehyde (MDA) is both mutagenic and tumorigenic. Experimental and clinical studies have shown that a major mechanism for cytotoxic activity of the numerous chemotherapeutic agents is through increased formation of the reactive oxygen species. The chemotherapeutic agents such as cyclophosphamide (cytoxan), doxorubicin (adriamycin) now commonly used for treatment of breast cancer, have all been shown to increase lipid peroxidation and generation of ROS (Moradi et al, 2008).

Vaquero et al (2004) pointed out that one reason why pancreatic cancer is so aggressive and unresponsiveness to treatments is its resistance to apoptosis. They proposed that ROS are a prosurvival, antiapoptotic factor of pancreatic cancer cells. Human pancreatic adenocarcinoma cells generated ROS, which was stimulated by growth factors (serum, insulin-like growth factor I, or fibroblast growth factor-2). Pancreatic cancer cells were also characterized by enhanced NADPH oxidase activity which generates ROS.

Currently, only very limited reports on biomarkers for the detection of early stage cancers are available. For example, we have previously reported the use of a 16 amino acid peptide fragment from the 1,395 amino acid G protein coupled receptor-associated sorting protein 1 (Zheng et al, 2012; Chang and Tuszynski, 2013) as an early biomarker for breast cancer. People are regularly told to watch for early symptoms of cancer. However, by the time symptoms occur, many tumors have already grown quite large and may have metastasized. Moreover, many cancers such as pancreatic and prostate cancers have no symptoms. There remains a pressing need for biomarkers of early stage and late stage cancer to enable the detection, diagnosis, and treatment of cancer at its earliest stages of development, as well as its later stages of development.

SUMMARY OF THE INVENTION

The present invention pertains to serum biomarkers for diagnosis of cancer comprising at least one stabilized cancer peptide fragment from "redoxin proteins" selected from the group consisting of thioredoxin; peroxiredoxin-1, 2 and 3; glutaredoxin-3; glutathione peroxidase-4; and nucleoredoxins.

In one embodiment of the present invention an in vitro method comprises comparing the expression level of one said cancer peptide biomarker comprising, consisting essentially of, or consisting of an amino acid sequence selected from the group consisting of SEQ ID NO: 1 to 42 in an individual suspected to suffer from cancer and/or to be susceptible to cancer to the expression level in a healthy individual. In another embodiment of the present invention an in vitro method comprises comparing the expression levels of a plurality of cancer peptide fragments comprising, consisting essentially of, or consisting of an amino acid sequence selected from the group consisting of SEQ ID NO: 1 to 42 in an individual suspected to suffer from cancer and/or to be susceptible to cancer to the expression levels in a healthy individual. In a more preferred embodiment of the in vitro method, an increase of the expression levels of said markers is indicative of cancer or the susceptibility to cancer.

According to particular embodiments, the accuracy of the diagnosis of cancer can be increased by analyzing combinations of multiple cancer peptides comprising, consisting essentially of, or consisting of an amino acid sequence selected from the group consisting of SEQ ID NO: 1 to 42. Thus, the in vitro method herein comprises at least two, preferably at least three, more preferably at least four, even more preferably at least five of the polypeptides listed from the group consisting of SEQ ID NO: 1 to 42.

In yet another embodiment, the present invention provides a method for assessing the severity or aggressiveness of cancer based on expression levels of a serum cancer peptide fragment or a plurality of cancer peptide fragments selected from the group consisting of SEQ ID NO: 1 to 42. In another embodiment, the present invention provides a method for assessing the effectiveness of therapeutic intervention cancer based on expression levels of a serum cancer peptide fragment or a plurality of cancer peptide fragments selected from the group consisting of SEQ ID NO: 1 to 42 before and during treatment.

For diagnosis of pancreatic cancer, suitable biological samples to be analyzed for the presence or absence of a biomarker can be serum, plasma, pancreatic juice, cells of a pancreatic tumor, or cells of pancreatic tissue. Cells from pancreatic tissue can be obtained by ERCP, secretin stimulation, fine-needle aspiration, cytologic brushings and large-bore needle biopsy.

Another embodiment of the invention provides a biomolecule (e.g., an antibody or antibody fragment) that is selective for a redoxin peptide fragment, wherein the redoxin peptide fragment comprises, consists essentially of, or consists of an amino acid sequence selected from the group consisting of SEQ ID NOS: 1-42.

Another embodiment of the invention provides a kit for diagnosing cancer in a subject, for determining whether a subject is predisposed to cancer, and/or for assessing the progression of cancer in a subject, the kit comprising one or more biomolecules (e.g., antibodies or antibody fragments), wherein each biomolecule is selective for a redoxin peptide fragment that comprises, consists essentially of, or consists of an amino acid sequence selected from the group consisting of SEQ ID NOS: 1-42. Another embodiment of the invention provides a method for determining whether cancer is present in a subject and/or whether a subject is predisposed to cancer, the method comprising determining whether one or more redoxin peptide fragments are present in a biological sample obtained from the subject, wherein each redoxin peptide fragment comprises, consists essentially of, or consists of an amino acid sequence selected from the group consisting of SEQ ID NOS: 1-42; wherein said determining is performed by contacting the biological sample with one or more biomolecules (e.g., antibodies or antibody fragments) selective for the one or more redoxin peptide fragments and detecting whether binding occurs between the one or more redoxin peptide fragments and the one or more biomolecules, wherein binding between the one or more redoxin peptide fragments and the one or more biomolecules indicates the presence of one or more redoxin peptide fragments in the biological sample; and wherein the presence of one or more redoxin peptide fragments in the biological sample indicates that cancer is present in the subject or that the subject is predisposed to cancer.

Another embodiment of the present invention provides a method for monitoring the progression of cancer in a subject comprising determining the amount of one or more redoxin peptide fragments present in the biological sample at a first time point, determining the amount of one or more redoxin peptide fragments present in the biological sample at one or more subsequent time points, and comparing the amount of the one or more redoxin peptide fragments present in the biological sample at the one or more subsequent time points with the amount of the one or more redoxin peptide fragments present in the biological sample at the first time point, wherein a higher amount of the one or more redoxin peptide fragments at the one or more subsequent time points compared to the amount of the one or more redoxin peptide fragments at the first time point indicates that the cancer has progressed since the first time point, and wherein a lower amount of the one or more redoxin peptide fragments at the one or more subsequent time points compared to the amount of the one or more redoxin peptide fragments at the first time point indicates that the cancer has regressed since the first time point, wherein each of the one or more redoxin peptide fragments comprises, consists essentially of, or consists of an amino acid sequence selected from the group consisting of SEQ ID NOS: 1-42.

Another embodiment of the present invention provides a method for treating cancer in a subject comprising administering to the subject an effective amount of one or more biomolecule that is selective for a peptide fragment comprising, consisting essentially of, or consisting of an amino acid sequence selected from the group consisting of SEQ ID NOS: 1-42.

BRIEF DESCRIPTION OF THE FIGURES

FIG. 2 illustrates an amino acid sequence comprising SEQ ID NO: 1.

FIG. 3 illustrates an amino acid sequence comprising SEQ ID NO: 7.

FIG. 4 illustrates an amino acid sequence comprising SEQ ID NO: 13.

FIG. 5 illustrates an amino acid sequence comprising SEQ ID NO: 19.

FIG. 6 illustrates an amino acid sequence comprising SEQ ID NO: 23.

FIG. 7 illustrates an amino acid sequence comprising SEQ ID NO: 27.

FIG. 8 illustrates amino acid sequences comprising SEQ ID NO: 32.

DETAILED DESCRIPTION OF THE INVENTION

Figure 1:
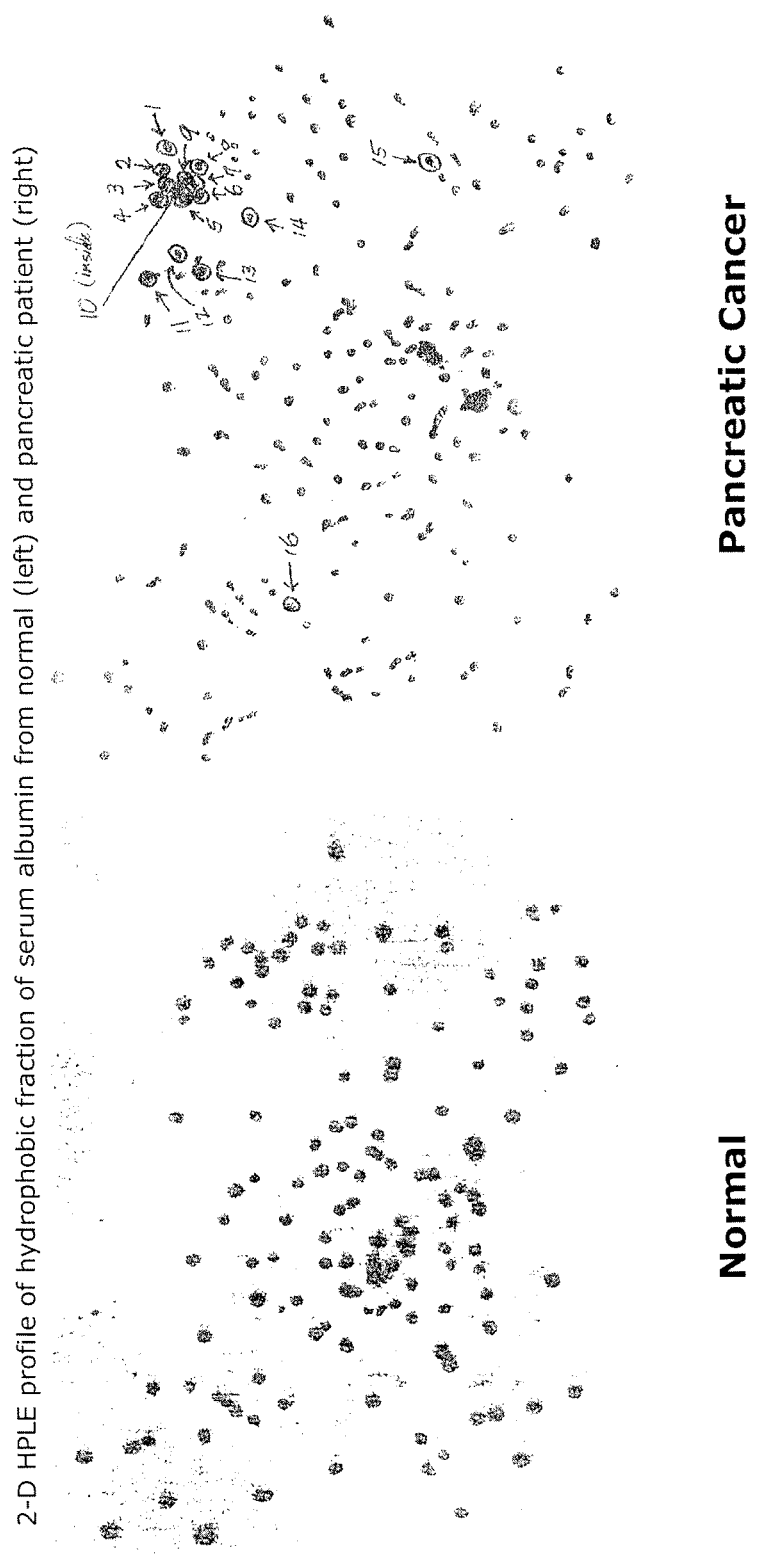
FIG. 1 illustrates 2-D HPLE profiles of a hydrophobic fraction of serum albumin complexes from a normal patient and a pancreatic cancer patient. A cluster of 10 albumin complexes at the upper right hand corner appears in all sera of pancreatic cancer patients. Sixteen spots were subjected to mass spectrometric analysis (LC-MS/MS) to identify the sequestered cancer peptide fragments. The numbers indicate the spots selected for mass spectrometric analysis.

The applicants have discovered stabilized cancer peptide fragments, referred to herein as "redoxin peptide fragments," that are found in biological samples obtained from cancer patients. According to particular embodiments of the present invention, the stabilized cancer peptide fragments can be used as biomarkers for detecting cancer in a subject, or for detecting a subject's predisposition to cancer. The cancer peptide fragments are derived from "redoxin proteins" in thioredoxin and glutaredoxin systems, which cancer cells use to defend themselves against high oxidative and hypoxic stresses. The redoxin proteins are thioredoxin; peroxiredoxin-1; peroxiredoxin-2; peroxiredoxin-3; glutaredoxin-3; glutathione peroxidase-4; and nucleoredoxins.

Even though many proteins are found to be over-produced in cancer cells (via either genomic or proteomic approaches) and constitute the so-called cancer biomarker protein repertoire, a vast majority of them have not been successfully used as serum biomarkers. One reason is because most of the reported cancer proteins are large molecules which are normally degraded to peptide fragments inside the cancer cell. As discussed herein, once released into the blood, these peptide fragments are subjected to further degradation with the resulting shorter peptide fragments later cleared from circulation by the kidneys (Lowenthal et al., 2005). Circulatory cancer peptide fragments have a short half-life of only about 2 to 4 hours which makes their detection highly variable and inconsistent when used as serum cancer biomarkers (Lowenthal et al., 2005). Compounding the problem further is the fact that sandwich ELISA is normally used for their detection. In sandwich ELISA, two antibodies directed against the same peptide (or protein) must be used. A capture antibody which recognizes a specific region of the peptide and a detection antibody recognizing a different epitope of the same peptide have to be generated. Due to the fact that it normally requires a peptide sequence of 10 to 15 amino acids for producing a specific antibody, the circulating peptide will need to have at least 25 to 30 amino acids to be useful for generating both the capture and detection antibodies. Most circulatory cancer peptides are likely to be shorter than 25 amino acids and even if they are longer peptides, their short half-life (less than 4 hours) will not allow for their consistent detection either.

Contrary to the "transient" nature of many circulatory peptide fragments in the blood, stabilized peptide fragments from over-produced cancer proteins can be developed into novel serum biomarkers. One way to find such stabilized peptide fragments is via their association with serum albumin. Only a very small fraction of peptide fragments originating from cancer proteins, if any, has high affinity for serum albumin and is sequestered by albumin. This association increases their blood half-life more than 100 fold over free circulating peptide fragments (Dennis et al., 2002). This sequestration by serum albumin makes cancer peptides stable and their detection very consistent rather than sporadic as in the case of free (unbound) circulatory peptides. Essentially, serum albumin acts as an affinity matrix for a limited number of cancer peptide fragments. A method for finding the stabilized (sequestered) cancer peptide fragments is to use a 2-D High Performance Liquid Electrophoresis (2-D HPLE) process which separates serum albumin complexes under non-denaturing conditions. 2-D HPLE technology described in WO 2011/008746 can cleanly separate about 400 serum albumin complexes circulating in the blood; of these, about 250 albumin complexes are in the hydrophilic fraction and 150 in the hydrophobic fraction. The hydrophobic fraction of serum albumin complexes was obtained via partition using Triton-X114 (Bordier, 1981). The separation of serum albumin complexes on polyvinylidene fluoride (PVDF) membrane also prevents the separated albumin complexes from diffusion as would have occurred with proteins separated by a polyacrylamide gel. Mass spectrometric analysis (LC-MS/MS) of the newly generated albumin complex reveals both the amino acid composition of the sequestered peptide fragment and equally importantly, the cancer protein it derived from. Thus, unlike the commonly used genomic or proteomic approaches which can only identify protein cancer biomarkers, the 2-D HPLE can accomplish two purposes: 1) finding new cancer biomarker proteins and 2) discovering the stabilized peptide fragments from the cancer proteins that can be used as new serum cancer biomarkers.

Using 2-D HPLE, the applicants analyzed serum samples from eleven pancreatic cancer patients and discovered that all pancreatic cancer patients exhibited practically identical profiles. Comparing to their normal individual counterparts, almost all of the differences (over 95%) are in the hydrophobic albumin complex fractions. A representative hydrophobic serum albumin profile for both normal and cancer patient is shown in FIG. 1. Many new albumin complexes appeared in cancer patients which were absent in normal (cancer-free) individuals. The applicants carried out mass spectrometric analysis (LC-MS/MS) of sixteen new serum albumin complex spots that appeared in cancer patients but were absent in normal (cancer-free) individuals.

Our Mass spectrometric analysis of the sixteen newly generated serum albumin spots revealed the presence of seven stabilized cancer peptide fragments from different serum albumin complexes. As discussed herein, the cancer peptide fragments are derived from proteins in both thioredoxin and glutaredoxin systems that cancer cells use to defend themselves against the high oxidative and hypoxic stresses. The "redoxin-proteins" are thioredoxin; peroxiredoxin-1, 2 and 3; glutaredoxin-3; glutathione peroxidase-4; and nucleoredoxins.

According to particular embodiments, the present invention provides a biomolecule that is selective for (i.e., that specifically binds to) a redoxin peptide fragment selected from the group consisting of SEQ ID NOS: 1-42. The redoxin peptide fragment may comprise, consist essentially of, or consist of any of the amino acid sequences of SEQ ID NOS: 1-42. The biomolecule may be, for example, an antibody (monoclonal or polyclonal) or an antibody fragment (e.g., a Fab fragment). For example, the biomolecule may be selected from the group consisting of a recombinant antibody, a recombinant monoclonal antibody, a polyclonal antibody, a humanized antibody and an antibody fragment.

The biomolecule is useful for diagnosing cancers that utilize redoxin proteins to eliminate ROS and/or oxidative stress; and is also useful for determining whether a subject is predisposed (susceptible) to cancers that utilize redoxin proteins to eliminate ROS and/or oxidative stress. For example, the biomolecule is useful for diagnosing cancer selected from the group consisting of breast cancer, colon cancer, endometrial carcinoma, esophagus squamous cell carcinoma, glioma, hepatocellular carcinoma, infiltrating ductal breast carcinoma, larynx cancer, lung squamous cell carcinoma, melanoma, mucinous cystadenocarcinoma of ovary, pancreatic cancer, prostate cancer, renal cell carcinoma, small bowel malignant stromal tumor, and stomach adenocarcinoma. According to preferred embodiments, the biomolecule is useful for diagnosing pancreatic cancer and/or for determining whether a subject is predisposed to pancreatic cancer.

Another embodiment of the present invention provides an array comprising a plurality of the biomolecules, which can be used to diagnose cancer and/or to determine whether a patient is predisposed to cancer.

Another embodiment of the present invention provides a composition comprising the biomolecule in a pharmaceutically acceptable carrier. Alternatively, a composition may comprise at least two biomolecules in a pharmaceutically acceptable carrier. As used herein, the term "pharmaceutically acceptable carrier" refers to a diluent, adjuvant, excipient, or vehicle with which a biomolecule (e.g., antibody) of the present invention is administered. Such carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when a compound is administered intravenously. Saline solutions and aqueous dextrose and glycerol solutions can also be employed as liquid carriers, particularly for injectable solutions. Suitable excipients include starch, glucose, lactose, sucrose, gelatin, silica gel, sodium stearate, glycerol monostearate, talc, sodium chloride, glycerol, propylene glycol, water, ethanol and the like. A pharmaceutically acceptable carrier can also include minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be included in a carrier. Methods for producing compounds in combination with carriers are known to those of skill in the art.

According to another embodiment, the present invention provides a kit for diagnosing cancer in a subject and/or for determining whether a subject is predisposed to cancer, the kit comprising: one or more biomolecules (preferably an antibody or antibody fragment) wherein each biomolecule is selective for a redoxin peptide fragment that comprises, consists essentially of, or consists of an amino acid sequence selected from the group consisting of SEQ ID NOS: 1-42. The kit is useful for diagnosing cancers that utilize redoxin proteins to eliminate ROS and/or oxidative stress and/or for determine whether a patient is predisposed to such cancers.

The kit may be used for diagnosing cancer selected from the group consisting of breast cancer, colon cancer, endometrial carcinoma, esophagus squamous cell carcinoma, glioma, hepatocellular carcinoma, infiltrating ductal breast carcinoma, larynx cancer, lung squamous cell carcinoma, melanoma, mucinous cystadenocarcinoma of ovary, pancreatic cancer, prostate cancer, renal cell carcinoma, small bowel malignant stromal tumor, and stomach adenocarcinoma. Preferably, the kit is used for diagnosing pancreatic cancer.

According to another embodiment of the present invention, a method for determining whether cancer is present in a subject (or whether a subject is predisposed to cancer) comprises determining whether one or more redoxin peptide fragments are present in a biological sample obtained from a subject, wherein each of the one or more redoxin peptide fragments comprises, consists essentially of, or consists of any of SEQ ID NOS: 1-42. The determining step is preferably performed by contacting the biological sample with one or more biomolecules (preferably an antibody or antibody fragment) selective for the one or more redoxin peptide fragments and detecting whether binding occurs between the one or more redoxin peptide fragments and the one or more biomolecules. The one or more biomolecules bind to an epitope that is present on the one or more redoxin peptide fragments that each biomolecule is specific for (e.g., an antibody specific for a redoxin peptide having amino acids of SEQ ID NO: 1 binds to an epitope on said redoxin peptide and/or an antibody specific for a redoxin peptide having amino acids of SEQ ID NO: 7 binds to an epitope on said redoxin peptide, etc.). Binding between the one or more redoxin peptide fragments and the one or more biomolecules indicates the presence of one or more redoxin peptide fragments in the biological sample. The presence of one or more redoxin peptide fragments in the biological sample indicates that cancer is present in the subject or that the subject is predisposed to cancer.

According to an alternative embodiment, the method comprises comparing the amount of the one or more redoxin peptide fragments in the biological sample to the amount of one or more redoxin peptide fragments in a biological sample from a cancer-free subject, wherein a higher amount of one or more redoxin peptide fragments in the biological sample compared to the amount of one or more redoxin peptide fragments in the biological sample from the cancer-free subject indicates that cancer is present in the subject or that the subject is predisposed to cancer.

The biological sample may comprise, for example, serum, plasma, cells of cancer tissues, fluids and the like. Non-limiting examples of fluids include blood, cerebro-spinal fluid, feces, gingival crevicular fluid, lachrymal fluid, lymph, perspiration, mammary gland secretions, mucus, saliva, semen, sputum, synovial fluid, tears, urine, vaginal secretions, and vitreous humor, preferably blood and serum. When the cancer being detected is pancreatic cancer, the biological sample may be selected from pancreatic tissue, cells from a pancreatic tumor, and pancreatic juice.

The step of detecting whether binding occurs between the one or more redoxin peptide fragments and the one or more biomolecules may be performed by using either a immuno-histochemical (IHC) staining or an ELISA, such as a peptide ELISA, a competitive ELISA or a sandwich ELISA.

According to particular embodiments, the subject has not been diagnosed with cancer prior to performing said method. Alternatively, the subject has not been diagnosed with late stage cancer and the presence of one or more redoxin peptide fragments in the biological sample indicates the presence of early stage cancer in the subject. As used herein, "early stage cancer" includes any pre-cancerous state prior to late stage cancer, including but not limited to benign conditions (any non-cancerous abnormality that has the potential to develop into late stage cancer), conditions prior to invasive carcinoma, and/or conditions prior to the development of a cancerous tumor. With regard to breast cancer, for example, "early stage cancer" includes any pre-cancerous state prior to stage I, stage II, stage III, or stage IV cancer. Examples of early stage breast cancer include benign conditions (e.g., non-proliferative lesions, proliferative lesions without atypia, and proliferative lesions with atypia), dysplasia, and/or carcinoma in situ. With regard to cancers other than breast cancer (e.g., colon cancer, endometrial carcinoma, esophagus squamous cell carcinoma, glioma, hepatocellular carcinoma, infiltrating ductal breast carcinoma, larynx cancer, lung squamous cell carcinoma, melanoma, mucinous cystadenocarcinoma of ovary, pancreatic cancer, prostate cancer, renal cell carcinoma, small bowel malignant stromal tumor, or stomach adenocarcinoma), "early stage cancer" includes any pre-cancerous state prior to late stage cancer, such as those that correspond to stage I, stage II, stage III, or stage IV in breast cancer.

As used herein, "cancer-free" refers to a subject who is free of either early stage or late stage cancer, or to tissue of a subject that is free of either early stage or late stage cancer. A subject as used herein is preferably an animal, including but not limited to mammals, and most preferably human.

According to another embodiment of the present invention, a method for treating cancer in a subject comprises administering to the subject an effective amount of a biomolecule (preferably an antibody or antibody fragment) that is selective for a peptide fragment comprising, consisting essentially of, or consisting of an amino acid sequence selected from SEQ ID NOS: 1-42. The method may inhibit or arrest the progression of cancer in the subject and/or inhibit or arrest the progression of early stage cancer to late stage cancer.

As used herein, the term "effective amount" refers to those amounts that, when administered to a particular subject in view of the nature and severity of that subject's disease or condition will have a desired therapeutic effect, e.g., an amount which will cure, prevent, inhibit, or at least partially arrest or partially prevent the progression of cancer.

According to alternative embodiments, the method may comprise administering to the subject an effective amount of two or more biomolecules selective for a peptide fragment comprising, consisting essentially of, or consisting of an amino acid sequence selected from SEQ ID NOS: 1-42. The biomolecule(s) may be in a pharmaceutical carrier.

Another embodiment of the present invention provides a method for monitoring the progression of cancer in a subject (e.g., for assessing the effectiveness of a treatment regime or therapeutic agent) comprising determining the amount of one or more redoxin peptide fragments present in the biological sample at a first time point, determining the amount of one or more redoxin peptide fragments present in the biological sample at one or more subsequent time points, and comparing the amount of the one or more redoxin peptide fragments present in the biological sample at the one or more subsequent time points with the amount of the one or more redoxin peptide fragments present in the biological sample at the first time point. A higher amount of the one or more redoxin peptide fragments at the one or more subsequent time points compared to the amount of the one or more redoxin peptide fragments at the first time point indicates that the cancer has progressed (the amount or severity of cancer has increased) since the first time point. A lower amount of the one or more redoxin peptide fragments at the one or more subsequent time points compared to the amount of the one or more redoxin peptide fragments at the first time point indicates that the cancer has regressed since the first time point (the amount or severity of cancer has decreased). Each of the one or more redoxin peptide fragments comprises, consists essentially of, or consists of an amino acid sequence selected from SEQ ID NOS: 1-42.

The step(s) of determining the amount of one or more redoxin peptide fragments at the first time point and the one or more subsequent time points is preferably performed by contacting the biological sample with one or more biomolecules (preferably one or more antibodies or antibody fragments) selective for the one or more redoxin peptide fragments and detecting whether binding occurs between the one or more redoxin peptide fragments and the one or more biomolecules, wherein the one or more biomolecules bind to an epitope that is present on the one or more redoxin peptide fragments. The step(s) of determining may be performed by using an ELISA, preferably an ELISA that utilizes only one antibody instead of two or more antibodies, such as a peptide ELISA or a competitive ELISA.

According to particular embodiments, the first time point is prior to a treatment regimen and the one or more subsequent time points are during or after the treatment regimen, wherein the method monitors the effectiveness of the treatment regimen over time.

According to another embodiment of the present invention, a method of producing antibodies comprises administering a redoxin peptide fragment to an immunologically competent host in an amount effective to cause the host to generate antibodies specific for the redoxin peptide fragment, wherein the peptide fragment has an amino acid sequence that comprises, consists essentially of, or consists of a sequence selected from SEQ ID NOS: 1-42, and recovering antibodies from the host.

As discussed herein, antibodies raised against redoxin peptide fragments that comprise, consist essentially of, or consist of amino acid sequences selected from SEQ ID NOS: 1-42 are highly specific "peptide antibodies" recognizing only a small region of the redoxin cancer protein (rather than the entire protein). Because the antibodies are raised against a very small region (or unique region) and not to the whole protein, they will be highly specific and will generally not be able to cross-react with other protein in the body. Antibodies directed against an entire cancer protein will likely miss a specific cancer peptide motif and therefore render them ineffective (or much less effective) in detecting a particular cancer peptide fragment. Furthermore, therapeutic drugs targeting a short cancer peptide (or cancer peptide motif) sequence will be highly specific and will be expected to have much fewer side effects, if any. According to particular embodiments, when carrying out ELISA detection the biomolecules of the present invention are specific for (i.e., are capable of detecting in a biological sample) peptides consisting essentially of, or consisting of, an amino acid sequence selected from SEQ ID NOS: 1-42, but they are not specific for (i.e., are not capable of detecting in a biological sample) the entire protein from which the fragment originates.

EXAMPLES

Example 1. Stabilized Peptide Fragment from Thioredoxin

The thioredoxin system is composed of the redox-active protein thioredoxin, the enzyme thioredoxin reductase and NADPH (Karlenius and Tonissen, 2010). Thioredoxin expression was found to be increased in several primary cancers, including pancreatic and prostate cancers (Karlenius and Tonissen, 2010). In addition to protection against oxidative stress, the thioredoxin system plays an important role in many cellular functions, including redox control of transcription factors, synthesis of deoxyribonucleotides, and cell growth. The applicants discovered the following cancer peptide fragments from the thioredoxin system involved in both ROS and oxidative stresses.

A nine amino acid fragment VGEFSGANK (SEQ ID NO: 1) was found to be sequestered in a serum albumin complex from pancreatic cancer patients. It comes from amino acid residues 86 to 94 of the 105 amino acid protein, as shown in FIG. 2.

It should be pointed out that even though thioredoxin has been reported to be over-produced in many cancers, and its fragments have been suggested as cancer biomarkers, this nine amino acid peptide fragment has not previously been reported as a cancer biomarker. Without the knowledge of a stabilized peptide sequence, the probability of finding this specific fragment from thioredoxin is extremely low. Even though antibodies against thioredoxin are commercially available, they are not directed against the peptide fragment sequestered by serum albumin. For dealing with longer peptide sequences, sandwich ELISA using two antibodies is normally used. For detecting a short cancer peptide circulating in the blood a peptide ELISA or competitive ELISA using just one antibody is preferably employed.

This peptide sequence, VGEFSGANK (SEQ ID NO: 1), may be used to generate cancer peptide-specific biomolecules (e.g., antibodies or antibody fragments). The antibodies can be either polyclonal or monoclonal. Besides being used to detect the stabilized peptide fragment, the antibodies can also be used to detect the over-production of thioredoxin in cancer cell via immunohistochemical (IHC) staining. Because trypsin was used to digest the peptide fragment sequestered by serum albumin and this peptide fragment is both preceded and terminated with a "K" residue, it is likely that the actual thioredoxin peptide fragment sequestered by serum albumin is longer than the 9 amino acid detected. Normally, an epitope of 10 to 15 amino acids, or 10 to 20 amino acids is used to produce an antibody with high specificity, so this 9 amino acid peptide is preferably lengthened somewhat from either the N- or C-terminal end (or both). For example, the sequence used to produce a biomolecule (e.g., an antibody) may be XXXXXVGEFSGANKXXXXX (SEQ ID NO: 2), where X at positions 1-5 and 15-19 may be any naturally-occurring amino acid and up to ten of the amino acids may be absent (i.e., any one or all of the X amino acids may be present or absent).

For example, a peptide may include 2 amino acids each from both N- and C-terminal ends and the peptide for antibody production now becomes QKVGEFSGANKEK (SEQ ID NO: 3). To produce an antibody it may also be necessary to add a cysteine residue to either the N- or C-terminals for conjugation purpose. One example of the amino acid sequence for biomolecule (e.g., antibody) production is CQKVGEFSGANKEK (SEQ ID NO: 4). According to another example, the sequence used to produce a biomolecule (e.g., an antibody) may be CXXXXVGEFSGANKXXXXX (SEQ ID NO: 5), where X at positions 2-5 and 15-19 may be any naturally-occurring amino acid and up to nine of the amino acids may be absent (i.e., any one or all of the X amino acids may be present or absent). According to another example, the sequence used to produce a biomolecule (e.g., an antibody) may be XXXXXXVGEF- SGANKXXXXXC (SEQ ID NO: 6), where X at positions 1-6 and 16-20 may be any naturally-occurring amino acid and up to eleven of the amino acids may be absent (i.e., any one or all of the X amino acids may be present or absent). Preferably, a peptide sequence of SEQ ID NO: 4, 5 or 6 has 10 to 15 amino acids, or 10 to 20 amino acids.

Furthermore, for optimal antibody production it may also be preferable to add an acetyl group to the N-terminal amino acid and/or to convert the C-terminal amino acid into an amide.

The discovery of a stabilized thioredoxin peptide fragment circulating in the blood is significant. Besides pancreatic cancer, high levels of thioredoxin expression were also found in many cancer cells, including lung, cervix, colorectal, hepatocellular, gastric carcinomas, prostate, and breast cancer (Karlenius and Tonissen, 2010). The serum level of this thioredoxin peptide fragment may be a biomarker for the presence of these cancers. In the applicants' previous studies of over-produced cancer proteins, it was found that there is a direct correlation between the amount of over-produced protein inside a cancer cell and the serum level of stabilized peptide fragment as measured by competitive ELISA (Zhang et al., 2012). High level of thioredoxin expression in cancer cells will lead to increased level of the 9 amino acid fragment in the blood. Numerous studies have shown that high levels of thioredoxin expression in cancer cells correlate with highly invasive and metastatic tumor activity both in vitro and in vivo (Ceccarelli, et al., 2008; Chaiswing, et al., 2007). Thioredoxin was found to stimulate cell invasion in cancer cells by promoting overall matrix metalloproteinase (MMP) activity through preferentially inhibiting the MMP inhibitors (Farina et al., 2001). Similarly, expression studies have shown that highest levels of thioredoxin expression are in the most aggressive tumors isolated from patients diagnosed with either breast, melanoma, prostate or colorectal cancer (Karlenius and Tonissen, 2010). Another important observation is that the aggressiveness of many tumors can be correlated with their redox phenotypes, which is characterized by the degree of thioredoxin expression. All of the above findings suggest that measurement of the stabilized thioredoxin peptide levels will be a good indicator for the presence of cancer, its invasive and metastatic potential in these cancers. Furthermore, high levels of thioredoxin and other anti-oxidant proteins are also correlated with cells displaying resistance to various chemotherapeutic agents, including doxorubicin, cisplatin, docetaxel and tamoxifen (Karlenius and Tonissen, 2010). Therefore, measurement of the levels of this stabilized thioredoxin peptide fragment before and during treatment would indicate whether or not a therapeutic intervention is working.

Example 2. Stabilized Peptide Fragments from Peroxiredoxins 1 and 2

Among the protein targets for thioredoxin are the peroxiredoxins (Hanschmann et al, 2013). Peroxiredoxins are a family of enzymes that catalyze the reduction of hydrogen peroxide and hydroperoxides to water and alcohol, respectively (Hanschmann et al., 2013). Six peroxiredoxins (Prxs) categorized by their subcellular localization are reported; Prx 1, 2 and 6 are found in the cytoplasm, Prx 4 in the endoplasmic reticulum, Prx 3 in the mitochondria, and Prx 5 found in various compartments in the cell, including peroxisomes and mitochondria. The peroxiredoxin system is an important cellular defense system against oxidative stress, and mitochondria in cancer cells are known to contain high levels of peroxiredoxin-3.

Short stabilized peptide fragments from peroxiredoxin-1 and, peroxiredoxin-2 were found to be sequestered by serum albumin forming new albumin complexes. The stabilized peptide fragments from these peroxiredoxins can be used as new serum cancer biomarkers.

An 11 amino acid peptide fragment QITVNDLPVGR (SEQ ID NO: 7) from sequence 141 to 151 of peroxiredoxin-1 (or 2) was found to be sequestered by serum albumin in pancreatic cancer patients. See FIG. 3. Due to sequence homology between peroxiredoxins-1 and 2, this peptide sequence is also present in peroxiredoxin-2. Therefore, it is possible that this peptide fragment originated from the over-produced peroxiredoxin-2 in cancer cells.

Because it contains 11 amino acids, it can be used directly to generate biomolecules (e.g., antibodies) after adding a "C" to either the N- or C terminal. If C is added to the N-terminal, the sequence becomes CQITVNDLPVGR (SEQ ID NO: 8). If necessary, it can also be lengthened somewhat from either N- or C-terminal end (or both) to generate a synthetic peptide for antibody production. For example, the sequence used to produce a biomolecule (e.g., an antibody) may be XXXXQITVNDLPVGRXXXX (SEQ ID NO: 9), where X at positions 1-4 and 16-19 may be any naturally-occurring or artificial amino acid and up to eight of the amino acids may be absent (i.e., any one or all of the X amino acids may be present or absent). According to another example, the sequence used to produce a biomolecule (e.g., an antibody) may be CXXXQITVNDLPVGRXXXX (SEQ ID NO: 10), where X at positions 2-4 and 16-19 may be any naturally-occurring amino acid and up to seven of the amino acids may be absent (i.e., any one or all of the X amino acids may be present or absent). According to another example, the sequence used to produce a biomolecule (e.g., an antibody) may be XXXXQITVNDLPVGRXXXC (SEQ ID NO: 11), where X at positions 1-4 and 16-18 may be any naturally-occurring amino acid and up to seven of the amino acids may be absent (i.e., any one or all of the X amino acids may be present or absent). Preferably, a peptide sequence of SEQ ID NO: 9, 10 or 11 has 10 to 15 amino acids, or 10 to 20 amino acids. A representative sequence is CLRQITVNDLPVGRSV (SEQ ID NO: 12). The C residue is added for conjugational purpose.

An 18 amino acid peptide fragment KEGGLGPLNIPLLADVTR (SEQ ID NO: 13) from residues 92 to 109 of peroxiredoxin-2 was found to be sequestered by serum albumin in pancreatic cancer patients. See FIG. 4.

Because this peptide fragment has 18 amino acids, it may be used directly for biomolecules (e.g., antibodies) after adding a "C" to either N- or C-terminal end such as C CKEGGLGPLNIPLLADVTR (SEQ ID NO: 14) or KEGGLGPLNIPLLADVTRC (SEQ ID NO: 15). Alternatively, the peptide sequence used to produce a biomolecule (e.g., an antibody) may be CXKEGGLGPLNIPLLADVTR (SEQ ID NO: 16), where X at positions 2 may be any naturally-occurring amino acid. Alternatively, the peptide sequence may be divided and used to produce two antibodies for conducting a sandwich ELISA. The peptide sequence used to produce the first antibody may be XXXXXRKEGGLGPLN (SEQ ID NO: 17), where X at positions 1 to 5 may be any naturally-occurring amino acid and up to five of the amino acids may be absent (i.e., any one or all of the X amino acids may be present or absent). The peptide sequence used to produce the second antibody may be IPLLADVTRRXXXXX (SEQ ID NO: 18), where X at positions 11 to 15 may be any naturally-occurring amino acid and up to five of the amino acids may be absent (i.e., any one or all of the X amino acids may be present or absent). Preferably, a peptide sequence of SEQ ID NO: 16, 17 or 18 has 10 to 15 amino acids, or 10 to 20 amino acids.

Peroxiredoxins protect cells and tissues from oxidative damage through their peroxidase activities in cancer and innate immunity. Recent studies have shown that peroxiredoxins expressed in tumor cells play positive roles in their progression and/or metastasis in transplanted animals (Ishii, 2012). Different functions of peroxiredoxins are required for their progression/metastasis in vivo depending on tumor types.

Peroxiredoxin-1 suppresses oxidative stress-induced cell death through direct/indirect interactions with different types of kinases and enzymes that play key roles in regulation of cell death and/or apoptosis (Riddell et al., 2011). Peroxiredoxin-1 enhances tumor progression and its expression is elevated in various cancer tissues and cancer cell lines that are linked with poor clinical outcomes and diminished overall patient survival (Ishii, 2012). A recent study shows peroxiredoxin-1 enhances growth of prostate cancer cells through Toll-like receptor 4-dependent regulation of tumor vasculature (Riddell et al., 2011). The Prx1 expression levels also increased in prostate cancer tissues during tumor progression. Peroxiredoxin-2 suppresses apoptosis signal regulating kinase1 (ASK1) activation by reactive oxygen species (ROS) through its peroxidase activity by maintaining thioredoxin in a reduced state in neurons (Soga et al., 2012).

Example 3. Stabilized Peptide Fragment from Peroxiredoxin-3

The applicants have also discovered a 7 amino acid peptide LLSDLTK (SEQ ID NO: 19) to be sequestered by serum albumin in pancreatic cancer patients. This peptide is from residues 160 to 166 of the 256 amino acid peroxiredoxin-3 (also called thioredoxin-dependent peroxide reductase). See FIG. 5.

According to particular embodiments, a sequence used to produce an antibody or other biomolecule is XXXXXLLSDLTKXXXXX (SEQ ID NO: 20) where X at positions 1-5 and 13-17 may be any naturally-occurring amino acid and up to ten of the amino acids may be absent (i.e., any one or all of the X amino acids may be present or absent). Alternatively, the sequence used to produce an antibody may be CXXXXLLSDLTKXXXXX (SEQ ID NO: 21) where X at positions 2-5 and 13-17 may be any naturally-occurring amino acid and up to nine of the amino acids may be absent (i.e., any one or all of the X amino acids may be present or absent). Alternatively, the sequence used to produce an antibody may be XXXXXLLSDLTKXXXXC (SEQ ID NO: 22) where X at positions 1-5 and 13-16 may be any naturally-occurring amino acid and up to nine of the amino acids may be absent (i.e., any one or all of the X amino acids may be present or absent). Preferably, a peptide sequence of SEQ ID NO: 20, 21 or 22 has 10 to 15 amino acids, or 10 to 20 amino acids.

Like cytosolic Prx I and Prx II, mitochondrial Prx III is overexpressed in cancers such as hepatocellular carcinoma and breast cancer (Song et al., 2011). The overexpression of Prx III can protect cells against oxidative injury. Moreover, mitochondria are a major site of hydrogen peroxide generation in cells. Prx III prefers to scavenge hydrogen peroxide, which will be the target for up to 90% of $H_2O_2$. The mitochondrial Prx III antioxidant system being exclusively present in mitochondria has been suggested as a potential target for cancer therapy (Song et al., 2011).

Example 4. Stabilized Peptide Fragment from Glutaredoxin-3

In addition to stabilized peptide fragments originating from thioredoxin and thioredoxin-dependent peroxiredoxins above, the applicants have also found peptide fragments from redox-dependent proteins that use glutathione instead of thioredoxin to remove ROS. Substantial evidence indicates that the alteration of cellular redox status by glutaredoxin is a critical factor in tumorigenesis (Lillig, 2008).

A 10 amino acid peptide QEAKCGFSKQ (SEQ ID NO: 23) from residue 257 to 266 of the 335 amino acid glutaredoxin-3 was found to be sequestered by serum albumin in pancreatic cancer patients. See FIG. 6.

Because of the presence of a "C" residue in the middle of the peptide which may interfere with antibody production, a 12 amino acid sequence starting with the internal C may be used to generate antibodies. An example of a sequence for biomolecule (e.g., antibody) production is CGFSKQILEILN (SEQ ID NO: 24). Another example of a sequence for biomolecule (e.g., antibody) production is CGFSKQILEILNXXXXXX (SEQ ID NO: 25), where X at positions 13-18 may be any naturally-occurring amino acid and up to six of the amino acids may be absent (i.e., any one or all of the X amino acids may be present or absent). Another example of a sequence for biomolecule (e.g., antibody) production is FMKGNKQEAKC (SEQ ID NO: 26). Preferably, a peptide sequence of SEQ ID NO: 25 or 26 has 10 to 15 amino acids, or 10 to 20 amino acids.

There are four glutaredoxins in humans: glutaredoxin-1, glutaredoxin-2, glutaredoxin-3, and glutaredoxin-5. Glutaredoxin-1 and glutaredoxin-2 are respectively cytosolic and mitochondrial isoforms. Glutaredoxin-3 is a multi-domain monothiol glutaredoxin and glutaredoxin-5 is a single domain monothiol glutaredoxin located in the mitochondria.

Human glutaredoxin-3 (also named PICOT, TXNL-2, and HUSSY-22) has been implicated in various signaling pathways that lead to the activation of cancer cells (Lillig, 2008). Originally identified as an interaction partner of protein kinase C-θ, glutaredoxin-3 was reported to function, for instance, in the activation of T cells through inhibition of mitogen-activated kinase and nuclear factor-κB signaling, the attenuation of cardiac hypertrophy by inhibiting calcineurin-nuclear factor of activated T-cell signaling, and p53-dependent neuronal differentiation. These observations suggest that glutaredoxin-3 inhibits apoptosis via its role either in cell activation-associated signaling pathways or in the cellular response to stress signals. Glutaredoxin-3 protein has recently been suggested as a diagnostic biomarker for lung cancer and colorectal cancer for early diagnosis and prognosis of lung cancer and colorectal cancer (Kim, 2012). There is no report on the finding of stabilized glutaredoxin-3 peptide fragment circulating in the blood as cancer biomarker for pancreatic or other cancers.

Example 5. Stabilized Peptide Fragment from Glutathione Peroxidase-4

A 9 amino acid peptide EFAAGYNVK (SEQ ID NO: 27) from glutathione peroxidase-4 was found to be sequestered by serum albumin forming a new serum albumin complex detected by 2-D HPLE in pancreatic cancer patients. It came from amino acid residues 118 to 126 of this protein. See FIG. 7.

Because this peptide fragment was both preceded by and terminated with a K residue, it is likely to be longer than 9 amino acids when present in the cancer serum albumin complex isolated by 2-D HPLE technology. A synthetic peptide for producing antibody for detecting this glutathione peroxidase-4 fragment circulating in the blood (and also over-production of this protein in cancer cells) will need to be lengthened to about 10 to 15 amino acids or 10 to 20 amino acids. One possible synthetic peptide sequence is CEIKEFAAGYNVKFD (SEQ ID NO: 28). Another example of a peptide sequence for biomolecule (e.g., antibody) production is XXXXEFAAGYNVKFDXXXX (SEQ ID NO: 29), where X at positions 1-4 and 16-19 may be any naturally-occurring amino acid and up to eight of the amino acids may be absent (i.e., any one or all of the X amino acids may be present or absent). Another example of a peptide sequence for biomolecule (e.g., antibody) production is CXXXEFAAGYNVKFDXXXX (SEQ ID NO: 30), where X at positions 2-4 and 16-19 may be any naturally-occurring amino acid and up to seven of the amino acids may be absent (i.e., any one or all of the X amino acids may be present or absent). Another example of a peptide sequence for biomolecule (e.g., antibody) production is XXXXEFAAGYNVKFDXXXC (SEQ ID NO: 31), where X at positions 1-4 and 16-18 may be any naturally-occurring amino acid and up to seven of the amino acids may be absent (i.e., any one or all of the X amino acids may be present or absent). Preferably, a peptide sequence of SEQ ID NO: 29, 30 or 31 has 10 to 15 amino acids, or 10 to 20 amino acids.

Glutathione peroxidase is involved in protection against oxidative stress using glutathione as a substrate. At least seven glutathione peroxidases (GPX1 to 7) exist in mammalian cells (Utomo et al., 2004). They are cytoplasmic GPX1; gastrointestinal GPX2; secreted GPX3; phospholipid hydroperoxidase GPX4; epididymal GPX5; olfactory GPX6; and non-selenocysteine containing phospholipid hydroperoxidase GPX7. Glutathione peroxidase-3 has been implicated in several cancers including breast and colon cancers (Cole-Ezea et al., 2012).

Glutathione peroxidase-4 catalyzes the reduction of hydrogen peroxide, organic hydroperoxides, and lipid peroxides at the expense of reduced glutathione and functions in the protection of cells against oxidative stress. Glutathione peroxidase-4 differs from the other family members in terms of its monomeric structure, a less restricted dependence on glutathione as reducing substrate, and the ability to reduce lipid-hydroperoxides inside biological membranes. This protein is one of only a few proteins known in higher vertebrates to contain selenocysteine, which occurs at the active site of glutathione peroxidase and is coded by UGA that normally functions as a translation termination codon. It is localized predominantly in the cytosol. Glutathione peroxidase-4 has been shown to control both cyclooxygenases and lipooxygenases that exert substantial functions in tumor growth and angiogenesis (Schneider et al., 2010). There have been no reports indicating the over-expression of glutathione peroxidase-4 in pancreatic or prostate cancer. The stabilized fragment from glutathione peroxidase may be used as a biomarker for pancreatic cancer.

Example 6. Stabilized Peptide Fragment from Nucleoredoxin (Isoform X1)

In addition to thioredoxin and glutaredoxin systems above, the applicants have discovered a 17 amino acid peptide LYGIQDSEDDGESEAAK (SEQ ID NO: 32) from pancreatic cancer patients. See FIG. 8. Twelve of the 17 amino acids, DSEDDGESEAAK (SEQ ID NO: 36), came from residues 334-345 of the 435 amino acid of "Isoform 1" of nucleoredoxin (SEQ ID NO: 43). However, the first 5 amino acids, LYGIQ (SEQ ID NO: 46) came from residues 269 to 273 of the same protein. These two separated peptide fragments are also present in "Isoform 2" of nucleoredoxin which is a transcriptional variant of "Isoform 1". The two isoforms differ in the 5' UTR with "Isoform 2" lacking a portion of the 5' coding region, and initiating translation at an alternate start codon, compared to Isoform 1.

Interestingly, a different nucleoredoxin isoform (Isoform X1) was predicted from automated computational analysis derived from a genomic sequence (NT_010718.17) (NCBI Reference Sequence: XP_005256813.1) but has not been reported to be present. Isoform X1 apparently joins the two separated 5 and 12 amino acid fragments of Isoform 1 together to become 375 amino acids (or removing 60 amino acids from 435 amino acids Isoform 1).

The applicants' discovery of this contiguous 17 amino acid sequence provides the first evidence for the presence of "Isoform X1" of nucleoredoxin in pancreatic cancer patients. The normal nucleoredoxin (Isoform 1) has eight exons. It turns out that Isoform X1 skips exon 6 by joining exons 5 and 7 together resulting in a loss of 60 amino acids. Therefore, antibodies against either the 17 amino acid peptide fragment or a peptide fragment covering the two joined exons will detect not only the over-expression of nucleoredoxin isoform X1 in cancer cells, it may also be used to quantify the peptide fragment in serum samples from cancer patients using peptide or competitive ELISA. A suggested synthetic peptide for biomolecule (e.g., antibody) production may be CLYGIQDSEDDG (SEQ ID: 33) or LYGIQDSEDDGC (SEQ ID NO: 34). Alternatively, the sequence used to produce a biomolecule (e.g., an antibody) may be XXXXLYGIQDSEDDGXXXX (SEQ ID NO: 35), where X at positions 1-4 and 16-19 may be any naturally-occurring amino acid and up to eight of the amino acids may be absent (i.e., any one or all of the X amino acids may be present or absent).

On the other hand, if nucleoredoxin Isoforms 1 or 2 are over-expressed in other cancers, then the use of antibodies against the last 12 amino acid sequence DSEDDGESEAAK (SEQ ID NO: 36) will allow the detection of over-production of all isoforms containing this sequence. A suggested peptide sequence for biomolecule (e.g., antibody) production is CDSEDDGESEAAK (SEQ ID NO: 37). Alternatively, the sequence used to produce a biomolecule (e.g., an antibody) may be XXXXDSEDDGESEAAKXXXX (SEQ ID NO: 38), where X at positions 1-4 and 17-20 may be any naturally-occurring amino acid and up to eight of the amino acids may be absent (i.e., any one or all of the X amino acids may be present or absent). Alternatively, the sequence used to produce a biomolecule (e.g., an antibody) may be CXXXDSEDDGESEAAKXXXX (SEQ ID NO: 39), where X at positions 2-4 and 17-20 may be any naturally-occurring amino acid and up to seven of the amino acids may be absent (i.e., any one or all of the X amino acids may be present or absent). Alternatively, the sequence used to produce a biomolecule (e.g., an antibody) may be XXXXDSEDDGESEAAKXXXC (SEQ ID NO: 40), where X at positions 1-4 and 17-19 may be any naturally-occurring amino acid and up to seven of the amino acids may be absent (i.e., any one or all of the X amino acids may be present or absent). Alternatively, the sequence used to produce a biomolecule (e.g., an antibody) may be XLYGIQDSEDDGESEAAKX (SEQ ID NO: 41), where X at positions 1 and 19 may be any naturally-occurring amino acid and up to two of the amino acids may be absent (i.e., any one or all of the X amino acids may be present or absent). Alternatively, the sequence used to produce a biomolecule (e.g., an antibody) may be CXLY-GIQDSEDDGESEAAKX (SEQ ID NO: 42), where X at positions 2 and 20 may be any naturally-occurring amino acid and up to two of the amino acids may be absent (i.e., any one or all of the X amino acids may be present or absent). Preferably, a peptide sequence of SEQ ID NO: 37, 38, 39, 40, 41 or 42 has 10 to 15 amino acids, or 10 to 20 amino acids.

Nucleoredoxin was discovered as an oxidoreductase that contains a pair of redox-active Cys in its catalytic center. The original report indicated that nucleoredoxin mainly localizes in the nucleus, but it was later found that nucleoredoxin also exists in the cytoplasm. Nucleoredoxin was also identified as a major binding protein for dishevelled (Dvl), an essential mediator of Wnt signaling (Funato, 2010). Moreover, it was reported that nucleoredoxin stabilizes Dvl by inhibiting ubiquitination and degradation of Dvl. Therefore, nucleoredoxin is regarded as a bifunctional molecule to retain a pool of inactive Dvl for robust activation of Wnt signalling upon stimulation.

It is apparent that both ROS and oxidative stress are common features of solid tumors. Even though the above seven peptide fragments from seven different redoxin-proteins are detected in pancreatic cancer, some of them such as thioredoxin; peroxiredoxin-1, 2 and 3; glutaredoxin-3; and glutathione peroxidase-4 may also be present in other solid tumors to counteract the harmful effects of cellular ROS and oxidative stress.

Biomolecules specific for a peptide fragment having an amino acid sequence comprising, consisting essentially of, or consisting of SEQ ID NO: 1 to 42 may be useful for the detection of cancers and/or for assessing the progression of cancer and/or for assessing a treatment regimen, wherein the cancer is selected from the group consisting of breast cancer, colon cancer, endometrial carcinoma, esophagus squamous cell carcinoma, glioma, hepatocellular carcinoma, infiltrating ductal breast carcinoma, larynx cancer, lung squamous cell carcinoma, melanoma, mucinous cystadenocarcinoma of ovary, pancreatic cancer, prostate cancer, renal cell carcinoma, small bowel malignant stromal tumor, and stomach adenocarcinoma. According to particular embodiments, biomolecules specific for a peptide fragment having an amino acid sequence comprising, consisting essentially of, or consisting of SEQ ID NO: 1 to 42 may be useful for the detection and/or assessment of pancreatic cancer.

Due to its resistance to apoptosis, pancreatic cancer is particularly aggressive and unresponsive to treatments. The discovery of seven stabilized cancer peptide fragments in pancreatic cancer opens up the possibility for the development of a "pancreatic cancer biomarker panel" comprising two or more of these stabilized peptide fragments for detecting both the presence of pancreatic cancer and its severity based on the extent of their over-production in cancer cells.

An in vitro method for the diagnosis of cancers and/or the susceptibility to cancers can be developed comprising the steps of a) obtaining a biological sample; and b) detecting and/or measuring the increase levels of a stabilized cancer peptide fragments from at least one of the seven redoxin-proteins. The biological sample is derived from the group consisting of serum, plasma, cells of cancer tissues, fluids and the like from a subject. Non-limiting examples of fluids include blood, cerebro-spinal fluid, feces, gingival crevicular fluid, lachrymal fluid, lymph, perspiration, mammary gland secretions, mucus, saliva, semen, sputum, synovial fluid, tears, urine, vaginal secretions, and vitreous humor, preferably blood and serum. Cancer biomarker panels containing at least two antibodies against the seven redoxin-proteins can also be developed.

The expression level of serum peptide fragments in an individual suspected to suffer from cancer and/or to be susceptible to cancer will be higher compared to the expression levels of the same marker in a healthy individual due to the over-expression of redoxin-proteins in cancer cells. Since the aggressiveness of cancer is positively related to the production of redox-proteins in cancer cells, measurement of the stabilized serum peptide fragments released from these cancer proteins indicates the severity and invasiveness of cancers.

To quantify the serum cancer peptide fragment level, a competitive ELISA or a peptide ELISA may be used. An embodiment of a protocol for a competitive ELISA according to the present invention, using a single antibody against the peptide fragment, is provided below.

Experiments were carried out in triplicates. Two strip frames for inserting appropriate number of wells were prepared and name "plate A" and "plate B". Wells for both standards and samples on plate A were coated overnight with 300 ul of 1% bovine serum albumin (BSA) in PBS (pH7.4), at 4° C. Wells for both standards and samples on plate B were coated with 200 ul of peptide solution containing 100 ng of peptide in sodium carbonate buffer (pH 9.6), overnight at 4° C. 110 ul of standard solution ranging from 1, 2, 4, 6, 8, 16, 20, and 40 ng/ml and sample solutions to be analyzed were added to the BSA-coated plates. Both the samples and standards were in TSBT high salt (Tris-buffered saline with 0.05% Tween-20 and 0.5 M NaCl). After incubating for 30 min at room temperature, 110 ul of biotinylated anti-peptide antibody was added. The antibody was diluted 1:100,000 (1 ul antibody+99 ul TBST-High salt, take 20 ul and dilute into 20 ml TBST high salt.). After addition of the antibody solution, the final concentrations of standard solution become 0.5, 1, 2, 3, 4, 8, 10 and 20 ng/ml. The wells were shaken overnight at 4° C.

The next day, the unoccupied space from the peptide coated wells was blocked by coating them with 1% BSA by shaking at room temperature for 30 min. The wells were washed 5 times in 300 ul TBST high salt. 200 ul of antigen-antibody mixture from the BSA coated plate was transferred to peptide coated plate and shaking at room temperature for 1.5 h. This is followed by washing with 300 ul TBST high salt 5 times. Streptavidin-HRP (1:54,000 dilution in TBST high salt) was then added to the well (200 ul/well). After shaking at room temperature for 2 h, the wells were washed with 300 ul TBST high salt 5 times. This was followed by adding 100 ul TMB (tetramethylbenzidine, Pierce Chemical, Rockford. I L. USA). The wells were shaken at room temperature until O.D. 450 of TBST control (0 ng/ml in the standard curve) reaches 1.0. 1 M HCl (50 ul/well) was then added to the wells to stop the reaction. After reading at O.D.450, Prism 5.0 was used to generate the standard curve (one site-total function) and to calculate peptide concentrations of unknown samples.

An embodiment of a protocol for a peptide ELISA is provided below.

1) Immobilize patient serum by incubating 50 ul of a 1 to 10 dilution of patient sera (5 ul sera plus 45 ul phosphate buffered saline or PBS) in wells of a 96 well plate for 3 hours with shaking at room temp. 2) Aspirate and add 200 ul of a 3 percent hydrogen peroxide solution for 15 min with shaking at room temp to quench endogenous peroxidase activity. 3) Aspirate and block wells with 200 ul of 5 percent BSA in TBST with shaking for 30 min at room temp. 4) Aspirate and wash with 200 ul TBST with shaking at room temp. 5) Aspirate and add 100 ul of a 1 to 500 dilution of affinity purified primary antibody and incubate for 2 hours with shaking at room temperature. 6) Aspirate and wash wells 3 times each with 200 ul TBST. 7) Aspirate and add 1:3000 of goat anti-rabbit HRP antibody diluted in TBST containing 5 percent BSA. Incubate for 1 hour with shaking at room temp. 8) Aspirate and wash 3 times each with 200 ul TBST. 9) Develop with 100 ul of 1-STEP™ Ultra TMB for 30 min or until blue color forms. 10) Stop with 50 ul 1N $H_2SO_4$. 11) Read absorbance at 450 nm.

It is known that the aggressiveness of many cancers such as pancreatic cancer and their unresponsiveness to treatment is due to over-expression of redox-proteins that make them resistance to apoptosis. The above competitive and/or peptide ELISA can be used to quantify the serum level of stabilized peptide fragment (or levels of a number of redoxin-proteins) before treatment and during the treatment to assess the effectiveness of a therapeutical agent.

According to an embodiment, an antibody that binds specifically to a cancer polypeptide comprising, consisting essentially of, or consisting of a cancer peptide fragment having an amino acid sequence selected from SEQ ID NOS: 1-42, can be used to inhibit the growth of the cancer cell. A cancer biomarker array, comprising a plurality of antibodies, wherein each antibody binds specifically to a cancer polypeptide fragment comprising, consisting essentially of, or consisting of an amino acid sequence selected from SEQ ID NOS: 1-42 can be used to assess the presence, cancer severity and metastatic potential of different cancers.

Although the present invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the appended claims.

REFERENCES

Bordier, J. Phase separation of integral membrane proteins in Triton X-114 solution. (1981) J. Biol. Chem. 256: 1604-07.
Ceccarelli et al, The redox state of the lung cancer microenvironment depends on the levels of thioredoxin expressed by tumor cells and affects tumor progression and response to prooxidants. (2008) Int. J. Cancer 123: 1770-1778.
Chaiswing, et al., Characterization of redox state of two human prostate carcinoma cell lines with different degrees of aggressiveness. (2007) Free Radic. Biol. Med. 43: 202-215.
Chang F N, Yonan C R. System and methods for electrophoretic separation of proteins on protein binding membranes. (2008) U.S. Pat. No. 7,326,326.
Chang F N, Duong P, Tuszynski, G P. (2009) Method for detecting disease markers. WO/2009/014552.
Chang F N et al., Serum markers associated with early and late stages of breast cancer (2011). WO 2011/008746.
Chang F N and Tuszynski G P. G-protein coupled receptor-associated sorting protein 1 as a cancer biomarker. (2013) U.S. Pat. No. 8,420,333.
Cole-Ezea P, Swan D, Shanley D, Hesketh J. Glutathione peroxidase 4 has a major role in protecting mitochondria from oxidative damage and maintaining oxidative phosphorylation complexes in gut epithelial cells. (2012) Free Radic Biol Med. 53: 488-97.
Corthals G L, Wasinger V C, Hochstrasser D F, Sanchez J C. The dynamic range of protein expression: A challenge for proteomic research. (2000) Electrophoresis 21: 1104-1115.
Dennis M S, et al. Albumin binding as a general strategy for improving the pharmacokinetics of proteins. (2002) J. Biol. Chem. 277: 35035-43.
Dewhirst M W. Relationships between cycling hypoxia, HIF-1, angiogenesis and oxidative stress. (2009) Radiat Res. 172: 653-65.
Farina A R et al., Thioredoxin alters the matrix metalloproteinase/tissue inhibitors of metalloproteinase balance and stimulates human SK-N-SH neuroblastoma cell invasion. (2001) Eur J Biochem. 268: 405-13.
Funato Y et al., Nucleoredoxin Sustains Wnt/β-Catenin Signaling by Retaining a Pool of Inactive Dishevelled Protein. (2010) Current Biology 20: 1945-1952.
Hanschmann E M et al: Thioredoxins, Glutaredoxins, and Peroxiredoxins-MolecularMechanisms and Health Significance: From Cofactors to Antioxidants to Redox Signaling (2013) Antioxid Redox Signal. 219: 1539-605.
Lowenthal, M. S. et al., Analysis of albumin-associated peptide and proteins from ovarian cancer patients. (2005) Clinical Chemistry 51: 1933-45.
Merrell K, Southwick K, Graves S W, Esplin M S, Lewis N E, Thulin C D: Analysis of low-abundance, low-molecular-weight serum proteins using mass spectrometry. (2004) J. Biomol. Tech. 15: 238-248.
O'Farrell, P H. High resolution two-dimensional electrophoresis of proteins. (1975) J Biol Chem 250: 4007-21.
Ishii T, et al., Novel roles of peroxiredoxins in inflammation, cancer and innate immunity. (2012) J. Clin Biochem Nutr 50: 91-105.
Karlenius T C and Tonissen K Y. Thioredoxin and Cancer: A Role for Thioredoxin in all States of Tumor Oxygenatio (2010) Cancers 2: 209-232.
Lillig C H, Berndt C and Holmgren A, Glutaredoxin systems Biochimica et Biophysica Acta (BBA). (2008) 1780: 1304-1317.
Kim I H, Diagnosis or prognosis of lung cancer and colorectal cancer based on expression level of glutaredoxin 3. (2012) US 20120015847 A1.
Łuczaj W, Skrzydlewska E. DNA damage caused by lipid peroxidation products. (2003) Cell Mol Biol Lett. 8: 391-413.
Moradi M, Eftekhari M H and Talei A: Plasma Selenium Concentration and Glutathione Peroxidase Activity in Breast Cancer Patients Before and After Chemotherapy Iranian Journal of Cancer Prevention (2008) Vol 1, No 3, Summer 2.
Riddell J R et al: Peroxiredoxin 1 Controls Prostate Cancer Growth through Toll-Like Receptor 4 Dependent Regulation of Tumor Vasculature. (2011) Cancer Res. 71(5): 1637-1646.
Schneider M et al: Absence of Glutathione Peroxidase 4 Affects Tumor Angiogenesis through Increased 12/15-Lipoxygenase Activityl. (2010) Neoplasia 12: 254-263.
Song et al: Mitochondrial Peroxiredoxin III is a Potential Target for Cancer Therapy. (2011) Int. J. Mol. Sci. 12: 7163-7185.

Soga M et al., Oxidative Stress-Induced Diseases via the ASK1 Signaling Pathway. (2012) International Journal of Cell Biology, Article ID 439587, 5 pages.

Utomo A et al. Identification of a novel putative non-selenocysteine containing phospholipid hydroperoxide glutathione peroxidase (NPGPx) essential for alleviating oxidative stress generated from polyunsaturated fatty acids in breast cancer cells. (2004) J Biol Chem, 279: 43522-9.

Vaquero E C, et al. Reactive oxygen species produced by NAD(P)H oxidase inhibit apoptosis in pancreatic cancer cells. (2004) J Biol Chem, 279: 34643-54.

Vasseur et al, Hypoxia induced tumor metabolic switch contributes to pancreatic cancer aggressiveness. (2012) Cancers, 2: 2138-2152.

Zheng X et al., G-protein coupled receptor-associated sorting protein 1 (GASP-1), a ubiquitous tumor marker. (2012) Experimental and Molecular Pathology 93: 111-115.

---

What is claimed is:

1. A method for detecting one or more nucleoredoxin X1 peptide fragments in a biological sample obtained from a subject, wherein each nucleoredoxin X1 peptide fragment has the amino acid sequence of SEQ ID NO: 32, comprising
    (a) contacting the biological sample with one or more biomolecules selective for the amino acid sequence, wherein each biomolecule is selective for the amino acid sequence of SEQ ID NO: 32, and wherein each biomolecule is an antibody or a Fab fragment thereof, and
    (b) detecting whether binding occurs between the one or more nucleoredoxin X1 peptide fragments and the one or more biomolecules, wherein the binding between the one or more nucleoredoxin X1 peptide fragments and the one or more biomolecules indicates the presence of the one or more nucleoredoxin X1 peptide fragments in the biological sample.

2. The method of claim 1, wherein the biological sample is selected from the group consisting of serum, plasma, cells of cancer tissues, and fluids.

3. The method of claim 1, wherein the biological sample is selected from the group consisting of cells of pancreatic tissue, cells of a pancreatic tumor, and pancreatic juice.

4. The method of claim 1, wherein each biomolecule is a monoclonal antibody or a polyclonal antibody.

5. The method of claim 1, wherein detecting whether binding occurs between the one or more nucleoredoxin X1 peptide fragments and the one or more biomolecules is performed by using an immunohistochemical (IHC) staining or an ELISA.

6. The method of claim 1, wherein detecting whether binding occurs between the one or more nucleoredoxin X1 peptide fragments and the one or more biomolecules is performed by using a competitive ELISA, or a sandwich ELISA.

7. The method of claim 1, wherein the subject has not been diagnosed with cancer.

8. The method of claim 1, wherein the subject has not been diagnosed with late stage cancer.

* * * * *

SEQUENCE LISTING

```
<160> NUMBER OF SEQ ID NOS: 46

<210> SEQ ID NO 1
<211> LENGTH: 9
<212> TYPE: PRT
<213> ORGANISM: Artificial Sequence
<220> FEATURE:
<223> OTHER INFORMATION: Thioredoxin Variant

<400> SEQUENCE: 1

Val Gly Glu Phe Ser Gly Ala Asn Lys
1               5

<210> SEQ ID NO 2
<211> LENGTH: 19
<212> TYPE: PRT
<213> ORGANISM: Artificial Sequence
<220> FEATURE:
<223> OTHER INFORMATION: Thioredoxin Variant
<220> FEATURE:
<221> NAME/KEY: MISC_FEATURE
<222> LOCATION: (1)..(5)
<223> OTHER INFORMATION: Xaa at positions 1 to 5 may be any naturally-
      occurring or artificial amino acid and up to 5 of them may be
      absent
<220> FEATURE:
<221> NAME/KEY: MISC_FEATURE
<222> LOCATION: (15)..(19)
<223> OTHER INFORMATION: Xaa at positions 15 to 19 may be any naturally-
      occurring or artificial amino acid and up to 5 of them may be
      absent

<400> SEQUENCE: 2

Xaa Xaa Xaa Xaa Xaa Val Gly Glu Phe Ser Gly Ala Asn Lys Xaa Xaa
1               5                   10                  15

Xaa Xaa Xaa

<210> SEQ ID NO 3
<211> LENGTH: 13
<212> TYPE: PRT
<213> ORGANISM: Artificial Sequence
<220> FEATURE:
<223> OTHER INFORMATION: Thioredoxin Variant

<400> SEQUENCE: 3

Gln Lys Val Gly Glu Phe Ser Gly Ala Asn Lys Glu Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Thioredoxin Variant

<400> SEQUENCE: 4

Cys Gln Lys Val Gly Glu Phe Ser Gly Ala Asn Lys Glu Lys
```

```
<210> SEQ ID NO 5
<211> LENGTH: 19
<212> TYPE: PRT
<213> ORGANISM: Artificial Sequence
<220> FEATURE:
<223> OTHER INFORMATION: Thioredoxin Variant
<220> FEATURE:
<221> NAME/KEY: MISC_FEATURE
<222> LOCATION: (2)..(5)
<223> OTHER INFORMATION: Xaa at positions 2 to 5 may be any naturally-
      occurring or artificial amino acid and up to 4 of them may be
      absent
<220> FEATURE:
<221> NAME/KEY: MISC_FEATURE
<222> LOCATION: (15)..(19)
<223> OTHER INFORMATION: Xaa at positions 15 to 19 may be any naturally-
      occurring or artificial amino acid and up to 5 of them may be
      absent

<400> SEQUENCE: 5

Cys Xaa Xaa Xaa Xaa Val Gly Glu Phe Ser Gly Ala Asn Lys Xaa Xaa
1               5                   10                  15

Xaa Xaa Xaa

<210> SEQ ID NO 6
<211> LENGTH: 21
<212> TYPE: PRT
<213> ORGANISM: Artificial Sequence
<220> FEATURE:
<223> OTHER INFORMATION: Thioredoxin Variant
<220> FEATURE:
<221> NAME/KEY: MISC_FEATURE
<222> LOCATION: (1)..(6)
<223> OTHER INFORMATION: Xaa at positions 1 to 6 may be any naturally-
      occurring or artificial amino acid and up to 6 of them may be
      absent
<220> FEATURE:
<221> NAME/KEY: MISC_FEATURE
<222> LOCATION: (16)..(20)
<223> OTHER INFORMATION: Xaa at positions 16 to 20 may be any naturally-
      occurring or artificial amino acid and up to 5 of them may be
      absent

<400> SEQUENCE: 6

Xaa Xaa Xaa Xaa Xaa Xaa Val Gly Glu Phe Ser Gly Ala Asn Lys Xaa
1               5                   10                  15

Xaa Xaa Xaa Xaa Cys
            20

<210> SEQ ID NO 7
<211> LENGTH: 11
<212> TYPE: PRT
<213> ORGANISM: Artificial Sequence
<220> FEATURE:
<223> OTHER INFORMATION: Peroxiredoxin Variant

<400> SEQUENCE: 7

Gln Ile Thr Val Asn Asp Leu Pro Val Gly Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Peroxiredoxin Variant

<400> SEQUENCE: 8
```

Cys Gln Ile Thr Val Asn Asp Leu Pro Val Gly Arg
1               5                   10

<210> SEQ ID NO 9
<211> LENGTH: 19
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (1)..(4)
<223> OTHER INFORMATION: Xaa at positions 1 to 4 may be any naturally-
      occurring or artificial amino acid and up to 4 of them may be
      absent
<220> FEATURE:
<221> NAME/KEY: MISC_FEATURE
<222> LOCATION: (16)..(19)
<223> OTHER INFORMATION: Xaa at positions 16 to 19 may be any naturally-
      occurring or artificial amino acid and up to 4 of them may be
      absent

<400> SEQUENCE: 9

Xaa Xaa Xaa Xaa Gln Ile Thr Val Asn Asp Leu Pro Val Gly Arg Xaa
1               5                   10                  15

Xaa Xaa Xaa

<210> SEQ ID NO 10
<211> LENGTH: 19
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (2)..(4)
<223> OTHER INFORMATION: Xaa at positions 2 to 4 may be any naturally-
      occurring or artificial amino acid and up to 3 of them may be
      absent
<220> FEATURE:
<221> NAME/KEY: MISC_FEATURE
<222> LOCATION: (16)..(19)
<223> OTHER INFORMATION: Xaa at positions 16 to 19 may be any naturally-
      occurring or artificial amino acid and up to 4 of them may be
      absent

<400> SEQUENCE: 10

Cys Xaa Xaa Xaa Gln Ile Thr Val Asn Asp Leu Pro Val Gly Arg Xaa
1               5                   10                  15

Xaa Xaa Xaa

<210> SEQ ID NO 11
<211> LENGTH: 19
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (1)..(4)
<223> OTHER INFORMATION: Xaa at positions 1 to 4 may be any naturally-
      occurring or artificial amino acid and up to 4 of them may be
      absent
<220> FEATURE:
<221> NAME/KEY: MISC_FEATURE
<222> LOCATION: (16)..(18)
<223> OTHER INFORMATION: Xaa at positions 16 to 18 may be any naturally-
      occurring or artificial amino acid and up to 3 of them may be
      absent

<400> SEQUENCE: 11

```
Xaa Xaa Xaa Xaa Gln Ile Thr Val Asn Asp Leu Pro Val Gly Arg Xaa
1               5                   10                  15

Xaa Xaa Cys
```

<210> SEQ ID NO 12
<211> LENGTH: 16
<212> TYPE: PRT
<213> ORGANISM: Artificial Sequence
<220> FEATURE:
<223> OTHER INFORMATION: Peroxiredoxin Variant

<400> SEQUENCE: 12

```
Cys Leu Arg Gln Ile Thr Val Asn Asp Leu Pro Val Gly Arg Ser Val
1               5                   10                  15
```

<210> SEQ ID NO 13
<211> LENGTH: 18
<212> TYPE: PRT
<213> ORGANISM: Artificial Sequence
<220> FEATURE:
<223> OTHER INFORMATION: Peroxiredoxin Variant

<400> SEQUENCE: 13

```
Lys Glu Gly Gly Leu Gly Pro Leu Asn Ile Pro Leu Leu Ala Asp Val
1               5                   10                  15

Thr Arg
```

<210> SEQ ID NO 14
<211> LENGTH: 19
<212> TYPE: PRT
<213> ORGANISM: Artificial Sequence
<220> FEATURE:
<223> OTHER INFORMATION: Peroxiredoxin Variant

<400> SEQUENCE: 14

```
Cys Lys Glu Gly Gly Leu Gly Pro Leu Asn Ile Pro Leu Leu Ala Asp
1               5                   10                  15

Val Thr Arg
```

<210> SEQ ID NO 15
<211> LENGTH: 19
<212> TYPE: PRT
<213> ORGANISM: Artificial Sequence
<220> FEATURE:
<223> OTHER INFORMATION: Peroxiredoxin Variant

<400> SEQUENCE: 15

```
Lys Glu Gly Gly Leu Gly Pro Leu Asn Ile Pro Leu Leu Ala Asp Val
1               5                   10                  15

Thr Arg Cys
```

<210> SEQ ID NO 16
<211> LENGTH: 20
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (2)..(2)
<223> OTHER INFORMATION: Xaa at position 2 may be any naturally-
      occurring or artificial amino acid and may be absent

<400> SEQUENCE: 16

```
Cys Xaa Lys Glu Gly Gly Leu Gly Pro Leu Asn Ile Pro Leu Leu Ala
1               5                   10                  15

Asp Val Thr Arg
            20

<210> SEQ ID NO 17
<211> LENGTH: 15
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (1)..(5)
<223> OTHER INFORMATION: Xaa at positions 1 to 5 may be any naturally-
      occurring or artificial amino acid and up to 5 of them may be
      absent

<400> SEQUENCE: 17

Xaa Xaa Xaa Xaa Xaa Arg Lys Glu Gly Gly Leu Gly Pro Leu Asn
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (11)..(15)
<223> OTHER INFORMATION: Xaa at positions 11 to 15 may be any naturally-
      occurring or artificial amino acid and up to 5 of them may be
      absent

<400> SEQUENCE: 18

Ile Pro Leu Leu Ala Asp Val Thr Arg Arg Xaa Xaa Xaa Xaa Xaa
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Peroxiredoxin Variant

<400> SEQUENCE: 19

Leu Leu Ser Asp Leu Thr Lys
1               5

<210> SEQ ID NO 20
<211> LENGTH: 17
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (1)..(5)
<223> OTHER INFORMATION: Xaa at positions 1 to 5 may be any naturally-
      occurring or artificial amino acid and up to 5 of them may be
      absent
<220> FEATURE:
<221> NAME/KEY: MISC_FEATURE
<222> LOCATION: (13)..(17)
<223> OTHER INFORMATION: Xaa at positions 13 to 17 may be any naturally-
      occurring or artificial amino acid and up to 5 of them may be
      absent

<400> SEQUENCE: 20
```

```
Xaa Xaa Xaa Xaa Xaa Leu Leu Ser Asp Leu Thr Lys Xaa Xaa Xaa Xaa
1               5                   10                  15

Xaa
```

<210> SEQ ID NO 21
<211> LENGTH: 17
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (2)..(5)
<223> OTHER INFORMATION: Xaa at positions 2 to 5 may be any naturally-
      occurring or artificial amino acid and up to 4 of them may be
      absent
<220> FEATURE:
<221> NAME/KEY: MISC_FEATURE
<222> LOCATION: (13)..(17)
<223> OTHER INFORMATION: Xaa at positions 13 to 17 may be any naturally-
      occurring or artificial amino acid and up to 5 of them may be
      absent

<400> SEQUENCE: 21

```
Cys Xaa Xaa Xaa Xaa Leu Leu Ser Asp Leu Thr Lys Xaa Xaa Xaa Xaa
1               5                   10                  15

Xaa
```

<210> SEQ ID NO 22
<211> LENGTH: 17
<212> TYPE: PRT
<213> ORGANISM: Artificial Sequence
<220> FEATURE:
<223> OTHER INFORMATION: Peroxiredoxin Variant
<220> FEATURE:
<221> NAME/KEY: MISC_FEATURE
<222> LOCATION: (1)..(5)
<223> OTHER INFORMATION: Xaa at positions 1 to 5 may be any naturally-
      occurring or artificial amino acid and up to 5 of them may be
      absent
<220> FEATURE:
<221> NAME/KEY: MISC_FEATURE
<222> LOCATION: (13)..(16)
<223> OTHER INFORMATION: Xaa at positions 13 to 16 may be any naturally-
      occurring or artificial amino acid and up to 4 of them may be
      absent

<400> SEQUENCE: 22

```
Xaa Xaa Xaa Xaa Xaa Leu Leu Ser Asp Leu Thr Lys Xaa Xaa Xaa Xaa
1               5                   10                  15

Cys
```

<210> SEQ ID NO 23
<211> LENGTH: 10
<212> TYPE: PRT
<213> ORGANISM: Artificial Sequence
<220> FEATURE:
<223> OTHER INFORMATION: Glutaredoxin Variant

<400> SEQUENCE: 23

```
Gln Glu Ala Lys Cys Gly Phe Ser Lys Gln
1               5                   10
```

<210> SEQ ID NO 24
<211> LENGTH: 12
<212> TYPE: PRT
<213> ORGANISM: Artificial Sequence
<220> FEATURE:
<223> OTHER INFORMATION: Glutaredoxin Variant

<400> SEQUENCE: 24

Cys Gly Phe Ser Lys Gln Ile Leu Glu Ile Leu Asn
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Glutaredoxin Variant
<220> FEATURE:
<221> NAME/KEY: MISC_FEATURE
<222> LOCATION: (13)..(18)
<223> OTHER INFORMATION: Xaa at positions 13 to 18 may be any naturally-
      occurring or artificial amino acid and up to 6 of them may be
      absent

<400> SEQUENCE: 25

Cys Gly Phe Ser Lys Gln Ile Leu Glu Ile Leu Asn Xaa Xaa Xaa Xaa
1               5                   10                  15

Xaa Xaa

<210> SEQ ID NO 26
<211> LENGTH: 11
<212> TYPE: PRT
<213> ORGANISM: Artificial Sequence
<220> FEATURE:
<223> OTHER INFORMATION: Glutaredoxin Variant

<400> SEQUENCE: 26

Phe Met Lys Gly Asn Lys Gln Glu Ala Lys Cys
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Glutathione Peroxidase Variant

<400> SEQUENCE: 27

Glu Phe Ala Ala Gly Tyr Asn Val Lys
1               5

<210> SEQ ID NO 28
<211> LENGTH: 15
<212> TYPE: PRT
<213> ORGANISM: Artificial Sequence
<220> FEATURE:
<223> OTHER INFORMATION: Glutathione Peroxidase Variant

<400> SEQUENCE: 28

Cys Glu Ile Lys Glu Phe Ala Ala Gly Tyr Asn Val Lys Phe Asp
1               5                   10                  15

<210> SEQ ID NO 29
<211> LENGTH: 19
<212> TYPE: PRT
<213> ORGANISM: Artificial Sequence
<220> FEATURE:
<223> OTHER INFORMATION: Glutathione Peroxidase Variant
<220> FEATURE:
<221> NAME/KEY: MISC_FEATURE
<222> LOCATION: (1)..(4)
<223> OTHER INFORMATION: Xaa at positions 1 to 4 may be any naturally-
      occurring or artificial amino acid and up to 4 of them may be
      absent

```
<220> FEATURE:
<221> NAME/KEY: MISC_FEATURE
<222> LOCATION: (16)..(19)
<223> OTHER INFORMATION: Xaa at positions 16 to 19 may be any naturally-
      occurring or artificial amino acid and up to 4 of them may be
      absent

<400> SEQUENCE: 29

Xaa Xaa Xaa Xaa Glu Phe Ala Ala Gly Tyr Asn Val Lys Phe Asp Xaa
1               5                   10                  15

Xaa Xaa Xaa

<210> SEQ ID NO 30
<211> LENGTH: 19
<212> TYPE: PRT
<213> ORGANISM: Artificial Sequence
<220> FEATURE:
<223> OTHER INFORMATION: Glutathione Peroxidase Variant
<220> FEATURE:
<221> NAME/KEY: MISC_FEATURE
<222> LOCATION: (2)..(4)
<223> OTHER INFORMATION: Xaa at positions 2 to 4 may be any naturally-
      occurring or artificial amino acid and up to 3 of them may be
      absent
<220> FEATURE:
<221> NAME/KEY: MISC_FEATURE
<222> LOCATION: (16)..(19)
<223> OTHER INFORMATION: Xaa at positions 16 to 19 may be any naturally-
      occurring or artificial amino acid and up to 4 of them may be
      absent

<400> SEQUENCE: 30

Cys Xaa Xaa Xaa Glu Phe Ala Ala Gly Tyr Asn Val Lys Phe Asp Xaa
1               5                   10                  15

Xaa Xaa Xaa

<210> SEQ ID NO 31
<211> LENGTH: 19
<212> TYPE: PRT
<213> ORGANISM: Artificial Sequence
<220> FEATURE:
<223> OTHER INFORMATION: Glutathione Peroxidase Variant
<220> FEATURE:
<221> NAME/KEY: MISC_FEATURE
<222> LOCATION: (1)..(4)
<223> OTHER INFORMATION: Xaa at positions 1 to 4 may be any naturally-
      occurring or artificial amino acid and up to 4 of them may be
      absent
<220> FEATURE:
<221> NAME/KEY: MISC_FEATURE
<222> LOCATION: (16)..(18)
<223> OTHER INFORMATION: Xaa at positions 16 to 18 may be any naturally-
      occurring or artificial amino acid and up to 3 of them may be
      absent

<400> SEQUENCE: 31

Xaa Xaa Xaa Xaa Glu Phe Ala Ala Gly Tyr Asn Val Lys Phe Asp Xaa
1               5                   10                  15

Xaa Xaa Cys

<210> SEQ ID NO 32
<211> LENGTH: 17
<212> TYPE: PRT
<213> ORGANISM: Artificial Sequence
<220> FEATURE:
<223> OTHER INFORMATION: Nucleoredoxin Variant

<400> SEQUENCE: 32

Leu Tyr Gly Ile Gln Asp Ser Glu Asp Asp Gly Glu Ser Glu Ala Ala
```

```
1               5                   10                  15
Lys

<210> SEQ ID NO 33
<211> LENGTH: 12
<212> TYPE: PRT
<213> ORGANISM: Artificial Sequence
<220> FEATURE:
<223> OTHER INFORMATION: Nucleoredoxin Variant

<400> SEQUENCE: 33

Cys Leu Tyr Gly Ile Gln Asp Ser Glu Asp Asp Gly
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Nucleoredoxin Variant

<400> SEQUENCE: 34

Leu Tyr Gly Ile Gln Asp Ser Glu Asp Asp Gly Cys
1               5                   10

<210> SEQ ID NO 35
<211> LENGTH: 19
<212> TYPE: PRT
<213> ORGANISM: Artificial Sequence
<220> FEATURE:
<223> OTHER INFORMATION: Nucleoredoxin Variant
<220> FEATURE:
<221> NAME/KEY: MISC_FEATURE
<222> LOCATION: (1)..(4)
<223> OTHER INFORMATION: Xaa at positions 1 to 4 may be any naturally-
      occurring or artificial amino acid and up to 4 of them may be
      absent
<220> FEATURE:
<221> NAME/KEY: MISC_FEATURE
<222> LOCATION: (16)..(19)
<223> OTHER INFORMATION: Xaa at positions 16 to 19 may be any naturally-
      occurring or artificial amino acid and up to 4 of them may be
      absent

<400> SEQUENCE: 35

Xaa Xaa Xaa Xaa Leu Tyr Gly Ile Gln Asp Ser Glu Asp Asp Gly Xaa
1               5                   10                  15

Xaa Xaa Xaa

<210> SEQ ID NO 36
<211> LENGTH: 12
<212> TYPE: PRT
<213> ORGANISM: Artificial Sequence
<220> FEATURE:
<223> OTHER INFORMATION: Nucleoredoxin Variant

<400> SEQUENCE: 36

Asp Ser Glu Asp Asp Gly Glu Ser Glu Ala Ala Lys
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Nucleoredoxin Variant

<400> SEQUENCE: 37
```

```
Cys Asp Ser Glu Asp Asp Gly Glu Ser Glu Ala Ala Lys
1               5                   10
```

<210> SEQ ID NO 38
<211> LENGTH: 20
<212> TYPE: PRT
<213> ORGANISM: Artificial Sequence
<220> FEATURE:
<223> OTHER INFORMATION: Nucleoredoxin Variant
<220> FEATURE:
<221> NAME/KEY: MISC_FEATURE
<222> LOCATION: (1)..(4)
<223> OTHER INFORMATION: Xaa at positions 1 to 4 may be any naturally-
      occurring or artificial amino acid and up to 4 of them may be
      absent
<220> FEATURE:
<221> NAME/KEY: MISC_FEATURE
<222> LOCATION: (17)..(20)
<223> OTHER INFORMATION: Xaa at positions 17 to 20 may be any naturally-
      occurring or artificial amino acid and up to 4 of them may be
      absent

<400> SEQUENCE: 38

```
Xaa Xaa Xaa Xaa Asp Ser Glu Asp Asp Gly Glu Ser Glu Ala Ala Lys
1               5                   10                  15

Xaa Xaa Xaa Xaa
            20
```

<210> SEQ ID NO 39
<211> LENGTH: 20
<212> TYPE: PRT
<213> ORGANISM: Artificial Sequence
<220> FEATURE:
<223> OTHER INFORMATION: Nucleoredoxin Variant
<220> FEATURE:
<221> NAME/KEY: MISC_FEATURE
<222> LOCATION: (2)..(4)
<223> OTHER INFORMATION: Xaa at positions 2 to 4 may be any naturally-
      occurring or artificial amino acid and up to 3 of them may be
      absent
<220> FEATURE:
<221> NAME/KEY: MISC_FEATURE
<222> LOCATION: (17)..(20)
<223> OTHER INFORMATION: Xaa at positions 17 to 20 may be any naturally-
      occurring or artificial amino acid and up to 4 of them may be
      absent

<400> SEQUENCE: 39

```
Cys Xaa Xaa Xaa Asp Ser Glu Asp Asp Gly Glu Ser Glu Ala Ala Lys
1               5                   10                  15

Xaa Xaa Xaa Xaa
            20
```

<210> SEQ ID NO 40
<211> LENGTH: 20
<212> TYPE: PRT
<213> ORGANISM: Artificial Sequence
<220> FEATURE:
<223> OTHER INFORMATION: Nucleoredoxin Variant
<220> FEATURE:
<221> NAME/KEY: MISC_FEATURE
<222> LOCATION: (1)..(4)
<223> OTHER INFORMATION: Xaa at positions 1 to 4 may be any naturally-
      occurring or artificial amino acid and up to 4 of them may be
      absent
<220> FEATURE:
<221> NAME/KEY: MISC_FEATURE
<222> LOCATION: (17)..(19)
<223> OTHER INFORMATION: Xaa at positions 17 to 19 may be any naturally-
      occurring or artificial amino acid and up to 3 of them may be
      absent

<400> SEQUENCE: 40

Xaa Xaa Xaa Xaa Asp Ser Glu Asp Asp Gly Glu Ser Glu Ala Ala Lys
1               5                   10                  15

Xaa Xaa Xaa Cys
            20

<210> SEQ ID NO 41
<211> LENGTH: 19
<212> TYPE: PRT
<213> ORGANISM: Artificial Sequence
<220> FEATURE:
<223> OTHER INFORMATION: Nucleoredoxin Variant
<220> FEATURE:
<221> NAME/KEY: MISC_FEATURE
<222> LOCATION: (1)..(1)
<223> OTHER INFORMATION: Xaa at position 1 may be any naturally-
      occurring or artificial amino acid and may be absent
<220> FEATURE:
<221> NAME/KEY: MISC_FEATURE
<222> LOCATION: (19)..(19)
<223> OTHER INFORMATION: Xaa at position 19 may be any naturally-
      occurring or artificial amino acid and may be absent

<400> SEQUENCE: 41

Xaa Leu Tyr Gly Ile Gln Asp Ser Glu Asp Asp Gly Glu Ser Glu Ala
1               5                   10                  15

Ala Lys Xaa

<210> SEQ ID NO 42
<211> LENGTH: 20
<212> TYPE: PRT
<213> ORGANISM: Artificial Sequence
<220> FEATURE:
<223> OTHER INFORMATION: Nucleoredoxin Variant
<220> FEATURE:
<221> NAME/KEY: MISC_FEATURE
<222> LOCATION: (2)..(2)
<223> OTHER INFORMATION: Xaa at position 2 may be any naturally-
      occurring or artificial amino acid and may be absent
<220> FEATURE:
<221> NAME/KEY: MISC_FEATURE
<222> LOCATION: (20)..(20)
<223> OTHER INFORMATION: Xaa at position 20 may be any naturally-
      occurring or artificial amino acid and may be absent

<400> SEQUENCE: 42

Cys Xaa Leu Tyr Gly Ile Gln Asp Ser Glu Asp Asp Gly Glu Ser Glu
1               5                   10                  15

Ala Ala Lys Xaa
            20

<210> SEQ ID NO 43
<211> LENGTH: 435
<212> TYPE: PRT
<213> ORGANISM: Homo sapiens

<400> SEQUENCE: 43

Met Ser Gly Phe Leu Glu Glu Leu Leu Gly Glu Lys Leu Val Thr Gly
1               5                   10                  15

Gly Gly Glu Glu Val Asp Val His Ser Leu Gly Ala Arg Gly Ile Ser
                20                  25                  30

Leu Leu Gly Leu Tyr Phe Gly Cys Ser Leu Ser Ala Pro Cys Ala Gln
            35                  40                  45

Leu Ser Ala Ser Leu Ala Ala Phe Tyr Gly Arg Leu Arg Gly Asp Ala
        50                  55                  60

```
Ala Ala Gly Pro Gly Pro Gly Ala Gly Ala Ala Ala Glu Pro
65                  70                  75                  80

Glu Pro Arg Arg Arg Leu Glu Ile Val Phe Val Ser Ser Asp Gln Asp
            85                  90                  95

Gln Arg Gln Trp Gln Asp Phe Val Arg Asp Met Pro Trp Leu Ala Leu
            100                 105                 110

Pro Tyr Lys Glu Lys His Arg Lys Leu Lys Leu Trp Asn Lys Tyr Arg
            115                 120                 125

Ile Ser Asn Ile Pro Ser Leu Ile Phe Leu Asp Ala Thr Thr Gly Lys
            130                 135                 140

Val Val Cys Arg Asn Gly Leu Leu Val Ile Arg Asp Asp Pro Glu Gly
145                 150                 155                 160

Leu Glu Phe Pro Trp Gly Pro Lys Pro Phe Arg Glu Val Ile Ala Gly
                165                 170                 175

Pro Leu Leu Arg Asn Asn Gly Gln Ser Leu Glu Ser Ser Ser Leu Glu
            180                 185                 190

Gly Ser His Val Gly Val Tyr Phe Ser Ala His Trp Cys Pro Pro Cys
            195                 200                 205

Arg Ser Leu Thr Arg Val Leu Val Glu Ser Tyr Arg Lys Ile Lys Glu
210                 215                 220

Ala Gly Gln Asn Phe Glu Ile Ile Phe Val Ser Ala Asp Arg Ser Glu
225                 230                 235                 240

Glu Ser Phe Lys Gln Tyr Phe Ser Glu Met Pro Trp Leu Ala Val Pro
                245                 250                 255

Tyr Thr Asp Glu Ala Arg Arg Ser Arg Leu Asn Arg Leu Tyr Gly Ile
            260                 265                 270

Gln Gly Ile Pro Thr Leu Ile Met Leu Asp Pro Gln Gly Glu Val Ile
            275                 280                 285

Thr Arg Gln Gly Arg Val Glu Val Leu Asn Asp Glu Asp Cys Arg Glu
290                 295                 300

Phe Pro Trp His Pro Lys Pro Val Leu Glu Leu Ser Asp Ser Asn Ala
305                 310                 315                 320

Ala Gln Leu Asn Glu Gly Pro Cys Leu Val Leu Phe Val Asp Ser Glu
                325                 330                 335

Asp Asp Gly Glu Ser Glu Ala Ala Lys Gln Leu Ile Gln Pro Ile Ala
            340                 345                 350

Glu Lys Ile Ile Ala Lys Tyr Lys Ala Lys Glu Glu Ala Pro Leu
            355                 360                 365

Leu Phe Phe Val Ala Gly Glu Asp Asp Met Thr Asp Ser Leu Arg Asp
370                 375                 380

Tyr Thr Asn Leu Pro Glu Ala Ala Pro Leu Leu Thr Ile Leu Asp Met
385                 390                 395                 400

Ser Ala Arg Ala Lys Tyr Val Met Asp Val Glu Glu Ile Thr Pro Ala
                405                 410                 415

Ile Val Glu Ala Phe Val Asn Asp Phe Leu Ala Glu Lys Leu Lys Pro
            420                 425                 430

Glu Pro Ile
            435

<210> SEQ ID NO 44
<211> LENGTH: 327
<212> TYPE: PRT
<213> ORGANISM: Homo sapiens
```

-continued

<400> SEQUENCE: 44

Met Ala Asp Val Ser Leu His Arg Asn Pro Ala Thr Leu Lys Leu Trp
1               5                   10                  15

Asn Lys Tyr Arg Ile Ser Asn Ile Pro Ser Leu Ile Phe Leu Asp Ala
            20                  25                  30

Thr Thr Gly Lys Val Val Cys Arg Asn Gly Leu Leu Val Ile Arg Asp
        35                  40                  45

Asp Pro Glu Gly Leu Glu Phe Pro Trp Gly Pro Lys Pro Phe Arg Glu
    50                  55                  60

Val Ile Ala Gly Pro Leu Leu Arg Asn Asn Gly Gln Ser Leu Glu Ser
65                  70                  75                  80

Ser Ser Leu Glu Gly Ser His Val Gly Val Tyr Phe Ser Ala His Trp
                85                  90                  95

Cys Pro Pro Cys Arg Ser Leu Thr Arg Val Leu Val Glu Ser Tyr Arg
            100                 105                 110

Lys Ile Lys Glu Ala Gly Gln Asn Phe Glu Ile Ile Phe Val Ser Ala
        115                 120                 125

Asp Arg Ser Glu Glu Ser Phe Lys Gln Tyr Phe Ser Glu Met Pro Trp
    130                 135                 140

Leu Ala Val Pro Tyr Thr Asp Glu Ala Arg Arg Ser Arg Leu Asn Arg
145                 150                 155                 160

Leu Tyr Gly Ile Gln Gly Ile Pro Thr Leu Ile Met Leu Asp Pro Gln
                165                 170                 175

Gly Glu Val Ile Thr Arg Gln Gly Arg Val Glu Val Leu Asn Asp Glu
            180                 185                 190

Asp Cys Arg Glu Phe Pro Trp His Pro Lys Pro Val Leu Glu Leu Ser
    195                 200                 205

Asp Ser Asn Ala Ala Gln Leu Asn Glu Gly Pro Cys Leu Val Leu Phe
210                 215                 220

Val Asp Ser Glu Asp Asp Gly Glu Ser Glu Ala Ala Lys Gln Leu Ile
225                 230                 235                 240

Gln Pro Ile Ala Glu Lys Ile Ile Ala Lys Tyr Lys Ala Lys Glu Glu
                245                 250                 255

Glu Ala Pro Leu Leu Phe Phe Val Ala Gly Glu Asp Asp Met Thr Asp
            260                 265                 270

Ser Leu Arg Asp Tyr Thr Asn Leu Pro Glu Ala Ala Pro Leu Leu Thr
    275                 280                 285

Ile Leu Asp Met Ser Ala Arg Ala Lys Tyr Val Met Asp Val Glu Glu
290                 295                 300

Ile Thr Pro Ala Ile Val Glu Ala Phe Val Asn Asp Phe Leu Ala Glu
305                 310                 315                 320

Lys Leu Lys Pro Glu Pro Ile
                325

<210> SEQ ID NO 45
<211> LENGTH: 373
<212> TYPE: PRT
<213> ORGANISM: Homo sapiens

<400> SEQUENCE: 45

Met Ser Gly Phe Leu Glu Glu Leu Leu Gly Glu Lys Leu Val Thr Gly
1               5                   10                  15

Gly Gly Glu Glu Val Asp Val His Ser Leu Gly Ala Arg Gly Ile Ser
            20                  25                  30

```
Leu Leu Gly Leu Tyr Phe Gly Cys Ser Leu Ser Ala Pro Cys Ala Gln
             35                  40                  45

Leu Ser Ala Ser Leu Ala Ala Phe Tyr Gly Arg Leu Arg Gly Asp Ala
 50                  55                  60

Ala Ala Gly Pro Gly Pro Gly Ala Gly Ala Gly Ala Ala Ala Glu Pro
 65                  70                  75                  80

Glu Pro Arg Arg Arg Leu Glu Ile Val Phe Ser Ser Asp Gln Asp
                 85                  90                  95

Gln Arg Gln Trp Gln Asp Phe Val Arg Asp Met Pro Trp Leu Ala Leu
                100                 105                 110

Pro Tyr Lys Glu Lys His Arg Lys Leu Lys Leu Trp Asn Lys Tyr Arg
            115                 120                 125

Ile Ser Asn Ile Pro Ser Leu Ile Phe Leu Asp Ala Thr Thr Gly Lys
    130                 135                 140

Val Val Cys Arg Asn Gly Leu Leu Val Ile Arg Asp Asp Pro Glu Gly
145                 150                 155                 160

Leu Glu Phe Pro Trp Gly Pro Lys Pro Phe Arg Glu Val Ile Ala Gly
                165                 170                 175

Pro Leu Leu Arg Asn Asn Gly Gln Ser Leu Glu Ser Ser Ser Leu Glu
                180                 185                 190

Gly Ser His Val Gly Val Tyr Phe Ser Ala His Trp Cys Pro Pro Cys
            195                 200                 205

Arg Ser Leu Thr Arg Val Leu Val Glu Ser Tyr Arg Lys Ile Lys Glu
            210                 215                 220

Ala Gly Gln Asn Phe Glu Ile Ile Phe Val Ser Ala Asp Arg Ser Glu
225                 230                 235                 240

Glu Ser Phe Lys Gln Tyr Phe Ser Glu Met Pro Trp Leu Ala Val Pro
                245                 250                 255

Tyr Thr Asp Glu Ala Arg Arg Ser Arg Leu Asn Arg Leu Tyr Gly Ile
            260                 265                 270

Gln Asp Ser Glu Asp Asp Gly Glu Ser Glu Ala Ala Lys Gln Leu Ile
            275                 280                 285

Gln Pro Ile Ala Glu Lys Ile Ile Ala Lys Tyr Lys Glu Glu Ala
            290                 295                 300

Pro Leu Leu Phe Phe Val Ala Gly Glu Asp Asp Met Thr Asp Ser Leu
305                 310                 315                 320

Arg Asp Tyr Thr Asn Leu Pro Glu Ala Ala Pro Leu Leu Thr Ile Leu
                325                 330                 335

Asp Met Ser Ala Arg Ala Lys Tyr Val Met Asp Val Glu Glu Ile Thr
            340                 345                 350

Pro Ala Ile Val Glu Ala Phe Val Asn Asp Phe Leu Ala Glu Lys Leu
            355                 360                 365

Lys Pro Glu Pro Ile
    370

<210> SEQ ID NO 46
<211> LENGTH: 5
<212> TYPE: PRT
<213> ORGANISM: Homo sapiens

<400> SEQUENCE: 46

Leu Tyr Gly Ile Gln
 1               5
```